US007544826B2

(12) United States Patent
Mihan et al.

(10) Patent No.: US 7,544,826 B2
(45) Date of Patent: Jun. 9, 2009

(54) MONOCYCLOPENTADIENYL COMPLEXES

(75) Inventors: Shahram Mihan, Bad Soden (DE); Markus Enders, Heidelberg (DE); Pablo Fernandez, Dublin (IE)

(73) Assignee: Basell Polyolefine GmbH, Wesseling (DE)

( * ) Notice: Subject to any disclaimer, the term of this patent is extended or adjusted under 35 U.S.C. 154(b) by 27 days.

(21) Appl. No.: 10/583,204

(22) PCT Filed: Dec. 14, 2004

(86) PCT No.: PCT/EP2004/014226

§ 371 (c)(1),
(2), (4) Date: May 7, 2007

(87) PCT Pub. No.: WO2005/058928

PCT Pub. Date: Jun. 30, 2005

(65) Prior Publication Data

US 2007/0213484 A1    Sep. 13, 2007

Related U.S. Application Data

(60) Provisional application No. 60/543,360, filed on Feb. 10, 2004.

(30) Foreign Application Priority Data

Dec. 16, 2003  (DE) .............................. 103 59 341

(51) Int. Cl.
*C07F 17/00* (2006.01)
*C07F 11/00* (2006.01)
*B01J 31/00* (2006.01)

(52) U.S. Cl. ..................... 556/21; 556/43; 556/53; 556/110; 556/118

(58) Field of Classification Search .............. 556/43, 556/53, 21, 110, 118
See application file for complete search history.

(56) References Cited

U.S. PATENT DOCUMENTS

| 3,242,150 A | 3/1966 | Scoggin ............... 260/88.2 |
| 3,248,179 A | 4/1966 | Norwood ............... 23/285 |
| 3,709,853 A | 1/1973 | Karapinka ............ 260/88.2 D |
| 4,015,059 A | 3/1977 | Karol ................. 526/130 |
| 5,808,122 A | 9/1998 | Herrmann et al. ....... 556/58 |
| 6,255,418 B1 | 7/2001 | Jolly et al. ............ 526/160 |
| 6,417,302 B1 | 7/2002 | Bohnen ................. 526/160 |
| 6,437,161 B1 | 8/2002 | Mihan et al. ........... 556/11 |
| 6,451,938 B1 * | 9/2002 | Fisher et al. ............ 526/161 |
| 6,589,905 B1 | 7/2003 | Fischer et al. ........... 502/300 |
| 6,699,948 B2 | 3/2004 | Mihan et al. ........... 526/161 |
| 6,756,505 B1 | 6/2004 | Kristen et al. ........... 556/7 |
| 6,784,261 B1 | 8/2004 | Schopf et al. ........... 526/16 |
| 6,787,498 B2 | 9/2004 | Mihan et al. ........... 502/120 |
| 6,812,185 B2 | 11/2004 | Fischer et al. ........... 502/120 |
| 6,838,563 B2 | 1/2005 | Mihan et al. ........... 546/10 |
| 6,919,412 B1 | 7/2005 | Mihan et al. ........... 526/127 |
| 6,924,248 B2 | 8/2005 | Mihan et al. ........... 502/132 |
| 2003/0036658 A1 | 2/2003 | Miihan et al. ........... 548/402 |
| 2003/0036662 A1 | 2/2003 | Mihan et al. ........... 556/20 |
| 2003/0055267 A1 | 3/2003 | Mihan et al. ........... 548/402 |
| 2003/0176275 A1 | 9/2003 | Fraaije et al. ........... 502/103 |
| 2003/0236164 A1 | 12/2003 | Fischer et al. ........... 502/439 |
| 2004/0033890 A1 | 2/2004 | Mihan et al. ........... 502/113 |
| 2004/0214970 A1 | 10/2004 | Schopf et al. ........... 526/159 |
| 2004/0242880 A1 * | 12/2004 | Mihan et al. ........... 546/2 |
| 2007/0213205 A1 * | 9/2007 | Mihan ................... 502/113 |
| 2007/0213483 A1 * | 9/2007 | Mihan et al. ........... 526/126 |
| 2007/0213484 A1 * | 9/2007 | Mihan et al. ........... 526/160 |
| 2007/0255033 A1 * | 11/2007 | Kipke et al. ............ 526/352 |
| 2008/0064838 A1 * | 3/2008 | Mihan et al. ........... 526/204 |
| 2008/0097053 A1 * | 4/2008 | Mihan et al. ........... 526/126 |

FOREIGN PATENT DOCUMENTS

| DE | 19630580 | 2/1998 |
| DE | 19710615 | 9/1998 |
| EP | 742046 | 11/1996 |
| EP | 1212333 | 6/2002 |
| WO | 91/09882 | 7/1991 |
| WO | 96/00243 | 1/1996 |
| WO | 96/13529 | 5/1996 |
| WO | 97/04015 | 2/1997 |
| WO | 97/36937 | 10/1997 |
| WO | 98/22486 | 5/1998 |

(Continued)

OTHER PUBLICATIONS

M. Enders et al., "8-Quinolylcyclopentadienyl, a Ligand with a Tailored Fit for Chelate Complexes," *Chem. Ber.*, vol. 129, p. 459-463 (1996).
R. Halterman, "Synthesis and Applications of Chiral Cyclopentadienylmetal Complexes," *Chem. Rev.*, vol. 92(5), p. 965-994 (1992).
S. Strauss, "The Search for Larger and More Weakly Coordinating Anions," *Chem. Rev.*, vol. 93(3), p. 927-942 (1993).
Kirk-Othmer, "Olefin Polymers (High Pressure Polyethylene), High Pressure (Low and Intermediate Density) Polyethylene;" *Encyclopedia of Chemical Technology*, vol. 16, p. 402-420 (1981).
V. Gibson et al., "Novel Olefin polymerization catalysts based on iron and cobalt," *Chem. Commun.*, p. 849 (1998).
M. Brookhart et al., "Highly Active Iron and Cobalt Catalysts for the Polymerization of Ethylene," *J. Am. Chem. Soc.*, vol. 120(16), p. 4049-4050 (1998).

(Continued)

*Primary Examiner*—Porfirio Nazario Gonzalez
(74) *Attorney, Agent, or Firm*—Jarrod N. Raphael; Jonathan L. Schuchardt

(57) ABSTRACT

Monocyclopentadienyl complexes in which the cyclopentadienyl system bears at least one bridged donor and at least one aryl group and a catalyst system comprising at least one of the monocyclopentadienyl complexes, and also processes for preparing them, the use of the catalyst system for the polymerization or copolymerization of olefins and a process for preparing polyolefins by polymerization or copolymerization of olefins in the presence of the catalyst system and the preparation of the associated cyclopentadienyl system.

17 Claims, No Drawings

FOREIGN PATENT DOCUMENTS

| WO | 98/27124 | 6/1998 |
| --- | --- | --- |
| WO | 98/40419 | 9/1998 |
| WO | 99/06414 | 2/1999 |
| WO | 00/05277 | 2/2000 |
| WO | 00/24787 | 5/2000 |
| WO | 00/31090 | 6/2000 |
| WO | 00/35928 | 6/2000 |
| WO | 01/09148 | 2/2001 |
| WO | 01/12641 | 2/2001 |
| WO | 01/41920 | 6/2001 |
| WO | 01/92346 | 12/2001 |
| WO | 01/96417 | 12/2001 |
| WO | 03/024982 | 3/2003 |

OTHER PUBLICATIONS

H. Brinzinger et al., "*ansa*-Metallocene derivatives—XVII. Racemic and *meso* diastereomers of group IV metallocene derivatives with symmetrically substituted, dimethylsilanediyl-bridged ligand frameworks. Crystal structure of R,S-Me$_2$Si(3-t-Bu-5-MeC$_5$H$_2$)$_2$Zrcl$_2$," *Journal of Organometallic Chemistry*, vol. 369, p. 359-370 (1989).

P. Jutzi et al., "Cyclopentadienyl compounds with nitrogen donors in the side-chain," *Journal of Organometallic Chemistry 500*, p. 175-185 (1995).

L. Fieser & M. Fieser, Chapter 33, "Heterocyclen," *Lehrbuch der Organischen Chemie*, 3$^{rd}$ revised edition, Verlag Chemie, Weinheim (1957).

Lettau, *Chemie der Heterocyclen*, p. 17-27, 1$^{st}$ edition, VEB, Weinheim (1979).

L. Brandsma, "*Preparative Polar Organometallic Chemistry*," vol. 2, p. 133-142 (1991).

N. Furukawa et al., "Preparation of Pridyl Grignard Reagents and Cross Coupling Reactions with Sulfoxides Bearing Azaheterocycles," *Tetrahedron Letters*, vol. 28(47), p. 5845-5848 (1987).

*Chemical Reviews*, vol. 100(4), p. 1167-2476 (2000).

J. Ewen et al., "Expanding the Scope of Metallocene Catalysis: Beyond Indenyl and Fluorenyl Derivatives," *Springer Verlag*, p. 150-169 (1999).

"D. 7.3.5. Reaktionen mit metallorganischen Verbinungen," *Organikum*, 18$^{th}$ edition, p. 499 (1990).

S. Torkelson et al., "Silylation of 1,3-Dicarbonyl Compounds with Hexamethyldisilizane and Imidazole,"*Synthesis*, vol. 11, p. 722-724 (1976).

\* cited by examiner

MONOCYCLOPENTADIENYL COMPLEXES

The present invention relates to monocyclopentadienyl complexes in which the cyclopentadienyl system bears at least one bridged donor and at least one aryl group and to a catalyst system comprising at least one of the monocyclopentadienyl complexes, and also to processes for preparing them.

In addition, the invention provides for the use of the catalyst system for the polymerization or copolymerization of olefins and provides a process for preparing polyolefins by polymerization or copolymerization of olefins in the presence of the catalyst system and provides polymers obtainable in this way.

Many of the catalysts used for the polymerization of α-olefins are based on immobilized chromium oxides (cf., for example, Kirk-Othmer, "Encyclopedia of Chemical Technology", 1981, Vol. 16, p. 402). These generally give ethylene homopolymers and copolymers having high molecular weights but are relatively insensitive to hydrogen and thus do not allow the molecular weight to be controlled in a simple fashion. In contrast, the molecular weight of polyethylene can be controlled in a simple way by addition of hydrogen when using bis(cyclopentadienyl)chromium (U.S. Pat. No. 3,709,853), bis(indenyl)chromium or bis(fluorenyl)chromium (U.S. Pat. No. 4,015,059) applied to an inorganic, oxidic support.

As in the case of the Ziegler-Natta systems, there is now also a search for catalyst systems having a uniquely defined, active center, known as single site catalysts, in the case of the chromium compounds. The intention is to allow the activity, copolymerization behavior of the catalyst and the properties of the polymers obtained in this way to be altered in a simple fashion by target variation of the ligand framework.

DE 197 10615 describes monocyclopentadienylchromium compounds substituted by donor ligands which can be used for the polymerization of both ethene and propene. The donor is in this case from group 15 and uncharged. The donor is bound to the cyclopentadienyl ring via a $(ZR_2)_n$ fragment, where R is hydrogen, alkyl or aryl, Z is an atom of group 14 and n is $\geq 1$. DE 196 30 580 specifically claims Z=carbon in combination with an amine donor.

WO 96/13529 describes reduced transition metal complexes of elements of groups 4 to 6 of the Periodic Table with polydentate monoanionic ligands. These also include cyclopentadienyl ligands containing a donor function. The examples are restricted to titanium compounds.

WO01/12641 describes monocyclopentadienyl complexes of chromium, molybdenum and tungsten which bear, in particular, quinolyl or pyridyl donors which are bound either directly or via a $C_1$ or Si bridge to the cyclopentadienyl system.

WO 01/92346 discloses cyclopentadienyl complexes of elements of groups 4-6 of the Periodic Table of the Elements in which a dihydrocarbyl-Y group, where Y is an element of group 14 of the Periodic Table of the Elements, which bears particular Lewis bases is bound to the cyclopentadienyl system.

The abovementioned catalyst systems are not yet optimized in terms of their activities. Furthermore, the polymers and copolymers formed usually have very high molecular weights.

It is an object of the present invention to discover further transition metal complexes based on cyclopentadienyl ligands bearing a bridged donor which are suitable for the polymerization of olefins and display very high activities. A further object of the invention is to find an advantageous process for preparing such complexes.

We have found that this object is achieved by monocyclopentadienyl complexes comprising the structural feature of the formula $Cp-Y_mM^A$ (I), where the variables have the following meanings:
Cp is a cyclopentadienyl system having an aryl substituent,
Y is a substituent which is bound to Cp and contains at least one uncharged donor containing at least one atom of group 15 or 16 of the Periodic Table,
$M^A$ is titanium, zirconium, hafnium, vanadium, niobium, tantalum, chromium, molybdenum or tungsten or an element of group 3 of the Periodic Table and the lanthanides and
m is 1, 2 or 3.

Furthermore, we have found a catalyst system comprising the monocyclopentadienyl complexes of the present invention, the use of the monocyclopentadienyl complexes or of the catalyst system for the polymerization or copolymerization of olefins and a process for preparing polyolefins by polymerization or copolymerization of olefins in the presence of the monocyclopentadienyl complex or of the catalyst system and polymers obtainable in this way. Furthermore, a process and intermediates in this process have been found.

The monocyclopentadienyl complexes of the present invention comprise the structural element of the formula $Cp-Y_mM^A$ (I), where the variables are as defined above. Further ligands can consequently be bound to the metal atom $M^A$. The number of further ligands depends, for example, on the oxidation state of the metal atom. The ligands are not further cyclopentadienyl systems. Suitable ligands are monoanionic and dianionic ligands as described by way of example for X. In addition, Lewis bases such as amines, ethers, ketones, aldehydes, esters, sulfides or phosphines may be bound to the metal center M. The monocyclopentadienyl complexes can be in monomeric, dimeric or oligomeric form. The monocyclopentadienyl complexes are preferably in monomeric form.

$M^A$ is a metal selected from the group consisting of titanium, zirconium, hafnium, vanadium, niobium, tantalum, chromium, molybdenum and tungsten. The oxidation states of the transition metals $M^A$ in catalytically active complexes are usually known to those skilled in the art. Chromium, molybdenum and tungsten are very probably present in the oxidation state +3, titanium, zirconium, hafnium and vanadium in the oxidation state 4, with titanium and vanadium also being able to be present in the oxidation state 3. However, it is also possible to use complexes whose oxidation state does not correspond to that of the active catalyst. Such complexes can then be appropriately reduced or oxidized by means of suitable activators. $M^A$ is preferably titanium, vanadium, chromium, molybdenum or tungsten. Particular preference is given to chromium in the oxidation states 2, 3 and 4, in particular 3.

m can be 1, 2 or 3, i.e. 1, 2 or 3 donor groups Y can be bound to Cp. If 2 or 3 Y groups are present, these can be identical or different. Preference is given to only one donor group Y being bound to Cp (m=1).

The uncharged donor Y is an uncharged functional group containing an element of group 15 or 16 of the Periodic Table or a carbene, e.g. amine, imine, carboxamide, carboxylic ester, ketone (oxo), ether, thioketone, phosphene, phosphite, phosphine oxide, sulfonyl, sulfonamide, carbenes such as N-substituted imidazol-2-ylidene or unsubstituted, substituted or fused, partially unsaturated heterocyclic or heteroaromatic ring systems. The donor Y can be bound intermolecularly or intramolecularly to the transition metal $M^A$ or not be bound to it. Preference is given to the donor Y being bound intramolecularly to the metal center $M^A$. Particular preference is given to the monocyclopentadienyl complexes comprising the structural element of the formula $Cp-Y-M^A$.

Cp is a cyclopentadienyl system which can bear any substituents and/or be fused with one or more aromatic, aliphatic, heterocyclic or heteroaromatic rings, with 1, 2 or 3 substituents, preferably 1 substituent, being formed by the group Y and/or 1, 2 or 3 substituents, preferably 1 substituent, being substituted by the group Y and/or the aromatic, aliphatic, heterocyclic or heteroaromatic fused ring being 1, 2 or 3 substituents Y, preferably 1 substituent Y. Furthermore, the cyclopentadienyl system bears one or more aromatic substituents which are not fused to Cp and particularly preferably bears an aromatic substituent and/or the aromatic, aliphatic, heterocyclic or heteroaromatic fused ring bears 1, 2 or 3 aromatic substituents, preferably 1 aromatic substituent. The aromatic substituent is preferably bound to the cyclopentadienyl skeleton. The cyclopentadienyl skeleton itself is a $C_5$ ring system having 6 π-electrons, with one of the carbon atoms also being able to be replaced by nitrogen or phosphorus, preferably phosphorus. Preference is given to using $C_5$ ring systems which do not have a carbon atom replaced by a heteroatom. It is possible, for example, for a heteroaromatic containing at least one atom from the group consisting of N, P, O and S or an aromatic to be fused to this cyclopentadienyl skeleton. In this context, "fused to" means that the heterocycle and the cyclopentadienyl skeleton share two atoms, preferably carbon atoms. The cyclopentadienyl system is bound to $M^A$.

The aromatic substituent is preferably a $C_6$-$C_{22}$-aryl or alkylaryl having from 1 to 10 carbon atoms in the alkyl part and 6-20 carbon atoms in the aryl part, with the aromatic substituent also being able to be substituted by N—, P—, O— or S-containing substituents, $C_1$-$C_{22}$-alkyl, $C_2$-$C_{22}$-alkenyl, halogens or haloalkyls or haloaryls having 1-10 carbon atoms.

Particularly useful monocyclopentadienyl complexes are ones in which Y is formed by the group -$Z_k$-A- and together with the cyclopentadienyl system Cp and $M^A$ forms a monocyclopentadienyl complex comprising the structural element of the formula Cp-$Z_k$-A-$M^A$ (II), where the variables have the following meanings:

Cp-$Z_k$-A is

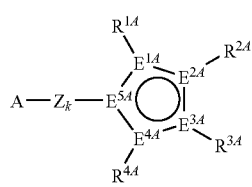

(III)

where the variables have the following meanings:
$E^{1A}$-$E^{5A}$ are each carbon or not more than one $E^{1A}$ to $E^{5A}$ is phosphorus,
$R^{1A}$-$R^{4A}$ are each, independently of one another, hydrogen, $C_1$-$C_{22}$-alkyl, $C_2$-$C_{22}$-alkenyl, $C_6$-$C_{22}$-aryl, alkylaryl having from 1 to 10 carbon atoms in the alkyl radical and 6-20 carbon atoms in the aryl radical, $NR^{5A}_2$, $N(SiR^{5A}_3)_2$, $OR^{5A}$, $OSiR^{5A}_3$, $SiR^{5A}_3$, $BR^{5A}_2$, where the organic radicals $R^{1A}$-$R^{4A}$ may also be substituted by halogens and two vicinal radicals $R^{1A}$-$R^{4A}$ may also be joined to form a five-, six- or seven-membered ring, and/or two vicinal radicals $R^{1A}$-$R^{4A}$ are joined to form a five-, six- or seven-membered heterocycle which contains at least one atom from the group consisting of N, P, O or S and at least one $R^{1A}$-$R^{4A}$ is a $C_6$-$C_{22}$-aryl, where the aryl may also be substituted by N—, P—, O— or S-containing substituents, $C_1$-$C_{22}$-alkyl, $C_2$-$C_{22}$-alkenyl, halogens or haloalkyls or haloaryls having 1-10 carbon atoms,
$R^{5A}$ the radicals $R^{5A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two geminal radicals $R^{5A}$ may also be joined to form a five- or six-membered ring,
Z is a divalent bridge between A and Cp selected from the group consisting of

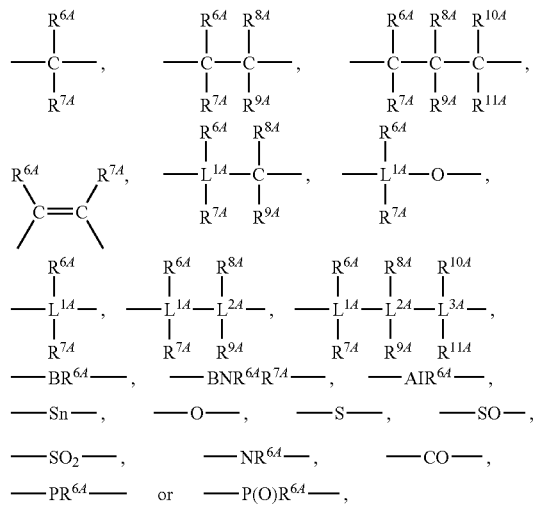

where
$L^{1A}$-$L^{3A}$ are each, independently of one another, silicon or germanium,
$R^{6A}$-$R^{11A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{12A}_3$, where the organic radicals $R^{6A}$-$R^{11A}$ may also be substituted by halogens and two geminal or vicinal radicals $R^{6A}$-$R^{11A}$ may also be joined to form a five- or six-membered ring and
$R^{12A}$ the radicals $R^{12A}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part, $C_1$-$C_{10}$-alkoxy or $C_6$-$C_{10}$-aryloxy and two radicals $R^{12A}$ may also be joined to form a five- or six-membered ring, and
A is an uncharged donor group containing one or more atoms of group 15 and/or 16 of the Periodic Table of the Elements or a carbene, preferably an unsubstituted, substituted or fused, heteroaromatic ring system,
$M^A$ is a metal selected from the group consisting of titanium in the oxidation state 3, vanadium, chromium, molybdenum and tungsten and
k is 0 or 1.

In preferred cyclopentadienyl systems Cp, all $E^{1A}$ to $E^{5A}$ are carbon.

The polymerization behavior of the metal complexes can be influenced by varying the substituents $R^{1A}$-$R^{4A}$. The type and number of the substituents can influence the ability of the olefins to be polymerized to gain access to the metal atom $M^A$. It is possible in this way to modify the activity and selectivity of the catalyst in respect of various monomers, in particular bulky monomers. Since the substituents can also influence the rate of termination reactions of the growing polymer chain, the molecular weight of the polymers being formed can also be altered in this way. One of the substituents $R^{1A}$-$R^{4A}$ is always a $C_6$-$C_{22}$-aryl or an alkylaryl having from 1 to 10 carbon atoms in the alkyl radical and 6-20 carbon atoms in the aryl radical in order to achieve the desired results. The remaining substituents can be varied widely. Examples of possible carboorganic substituents $R^{1A}$-$R^{4A}$ are the following: hydrogen, $C_1$-$C_{22}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_1$-$C_{10}$-alkyl group and/or a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{22}$-alkenyl which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{22}$-aryl which may be substituted by further alkyl groups, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, and arylalkyl which may be substituted by further alkyl groups, e.g. benzyl, o-, m-, p-methylbenzyl, 1- or 2-ethylphenyl, where two of the radicals $R^{1A}$ to $R^{4A}$ may also be joined to form a 5-, 6- or 7-membered ring and/or two of the vicinal radicals $R^{1A}$-$R^{4A}$ may be joined to form a five-, six- or seven-membered heterocycle which contains at least one atom from the group consisting of N, P, O or S and/or the organic radicals $R^{1A}$-$R^{4A}$ may also be substituted by halogens such as fluorine, chlorine or bromine. Furthermore, $R^{1A}$-$R^{4A}$ can also be amino $NR^{5A}_2$, or $N(SiR^{5A}_3)_2$, alkoxy or aryloxy $OR^{5A}$, for example dimethylamio, N-pyrrolidinyl, picolinyl, methoxy, ethoxy or isopropoxy. In organosilicon substituents $SiR^{5A}_3$, the radicals $R^{5A}$ can be the same carboorganic radicals as described in more detail above for $R^{1A}$-$R^{4A}$, where two $R^{5A}$ may also be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl. These $SiR^{5A}_3$ radicals can also be bound to the cyclopentadienyl skeleton via an oxygen or nitrogen, for example trimethylsilyloxy, trimethylsilyloxy, butyldimethylsilyloxy, tributylsilyloxy or tri-tert-butylsilyloxy. Preferred radicals $R^{1A}$-$R^{4A}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, ortho-dialkyl- or -dichloro-substituted phenyl, trialkyl- or trichloro-substituted phenyl, naphthyl, biphenyl and anthranyl. Particularly useful organosilicon substituents are trialkylsilyl groups having from 1 to 10 carbon atoms in the alkyl radical, in particular trimethylsilyl groups.

Two vicinal radicals $R^{1A}$-$R^{4A}$ together with the atoms $E^{1A}$-$E^{5A}$ bearing them form a heterocycle, preferably a heteroaromatic, which contains at least one atom from the group consisting of nitrogen, phosphorus, oxygen and sulfur, particularly preferably nitrogen and/or sulfur, with preference being given to the atoms $E^{1A}$-$E^{5A}$ present in the heterocycle or heteroaromatic being carbon. Preference is given to heterocycles and heteroaromatics having a ring size of 5 or 6 ring atoms. Examples of 5-membered heterocycles which have from one to four nitrogen atoms and/or a sulfur or oxygen atom in addition to carbon atoms as ring members are 1,2-dihydrofuran, furan, thiophene, pyrrole, isoxazole, 3-isothiazole, pyrazole, oxazole, thiazole, imidazole, 1,2,4-oxadiazole, 1,2,5-oxadiazole, 1,3,4-oxadiazole, 1,2,3-triazole and 1,2,4-triazole. Examples of 6-membered heteroaryl groups which may contain from one to four nitrogen atoms and/or a phosphorus atom are pyridine, phosphobenzene, pyridazine, pyrimidine, pyrazine, 1,3,5-triazine, 1,2,4-triazine or 1,2,3-triazine. The 5-membered and 6-membered heterocycles can also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine, dialkylamide, alkylarylamide, diarylamide, alkoxy or aryloxy or be fused with one or more aromatics or heteroaromatics. Examples of benzo-fused 5-membered heteroaryl groups are indole, indazole, benzofuran, benzothiophene, benzothiazole, benzoxazole and benzimidazole. Examples of benzo-fused 6-membered heteroaryl groups are chromane, benzopyran, quinoline, isoquinoline, cinnoline, phthalazine, quinazoline, quinoxaline, 1,10-phenanthroline and quinolizine. Naming and numbering of the heterocycles has been taken from Lettau, Chemie der Heterocyclen, 1$^{st}$ edition, VEB, Weinheim 1979. The heterocycles/heteroaromatics are preferably fused with the cyclopentadienyl skeleton via a C—C double bond of the heterocycle/heteroaromatic. Heterocycles/heteroaromatics having one heteroatom are preferably 2,3- or b-fused.

Cyclopentadienyl systems Cp having a fused heterocycle are, for example, thiapentalene, methylthiapentalene, ethylthiapentalene, isopropylthiapentalene, n-butylthiapentalene, tert-butylthiapentalene, trimethylsilylthiapentalene, phenylthiapentalene, naphthylthiapentalene, methylthiopentalene, azapentalene, methylazapentalene, ethylazapentalene, isopropylazapentalene, n-butylazapentalene, trimethylsilylazapentalene, phenylazapentalene, naphthylazapentalene, oxapentalene or phosphapentalene.

The synthesis of such cyclopentadienyl systems having a fused-on heterocycle is described, for example, in the above-mentioned WO 98/22486. In "metalorganic catalysts for synthesis and polymerisation", Springer Verlag 1999, Ewen et al., p. 150 ff, describe further syntheses of these cyclopentadienyl systems.

Particularly preferred substituents $R^{1A}$-$R^{4A}$ are the above-described carboorganic substituents and the carboorganic substituents which form a cyclic fused ring system, i.e. together with the $E^{1A}$-$E^{5A}$ skeleton, preferably together with a $C_5$cyclopentadienyl skeleton, form, for example, an unsubstituted or substituted indenyl, benzindenyl, phenanthrenyl or tetrahydroindenyl system, and in particular their preferred embodiments.

Examples of such cyclopentadienyl systems (without the group -Z-A-, which is preferably located in the 1 position, and without the aryl substituents) are monoalkylcyclopentadienyl systems, e.g. 3-methylcyclopentadienyl, 3-ethylcyclopentadienyl, 3-isopropylcyclopentadienyl, 3-tert-butylcyclopentadienyl, dialkylcyclopentadienyl systems, e.g. tetrahydroindenyl, 2,4-dimethylcyclopentadienyl or 3-methyl-5-tert-butylcyclopentadienyl, or trialkylcyclopentadienyl systems, e.g. 2,3,5-trimethylcyclopentadienyl, and also indenyl or benzoindenyl. The fused ring system may bear further $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{5A}_2$, $N(SiR^{5A}_3)_2$, $OR^{5A}$, $OSiR^{5A}_3$ or $SiR^{5A}_3$ substituents, e.g. 4-methylindenyl, 4-ethylindenyl, 4-isopropylindenyl, 5-methylindenyl, 4-phenylindenyl, 5-methyl-4-phenylindenyl or 4-naphthylindenyl.

One of the substituents $R^{1A}$-$R^{4A}$, preferably $R^{2A}$, is a $C_6$-$C_{22}$-aryl group or an alkylaryl group having from 1 to 10 carbon atoms in the alkyl part and 6-20 carbon atoms in the aryl part, preferably a $C_6$-$C_{22}$-aryl group such as phenyl, naphthyl, biphenyl, anthracenyl or phenanthrenyl, where the aryl may also be substituted by N-, P-, O- or S-containing substituents, $C_1$-$C_{22}$-alkyl, $C_2$-$C_{22}$-alkenyl, halogens or haloalkyls or haloaryls having 1-10 carbon atoms, for example o-, m-, p-methylphenyl, 2,3-, 2,4-, 2,5- or 2,6-dimethylphenyl, 2,3,4-, 2,3,5-, 2,3,6-, 2,4,5-, 2,4,6- or 3,4,5-trimethylphenyl, o-, m-, p-dimethylaminophenyl, o-, m-, p-methoxyphenyl, o-, m-, p-fluorophenyl, o-, m-, p-chlorophenyl, o-, m-, p-trifluoromethylphenyl, 2,3-, 2,4-, 2,5-, or 2,6-difluorophenyl, 2,3-, 2,4-, 2,5- or 2,6-dichlorophenyl or 2,3-, 2,4-, 2,5-, or 2,6-di(trifluoromethyl)phenyl. The N—, P—, O— or S-containing substituents, $C_1$-$C_{22}$-alkyl, $C_2$-$C_{22}$-alkenyl, halogens or haloalkyls or haloaryls having 1-10 carbon atoms as substituents on the aryl radical are preferably located in the para position relative to the bond to the cyclopentadienyl ring. The aryl substituent can be bound in the vicinal position to the substituent -Z-A or the two substituents are located in the 1,3 position relative to one another on the cyclopentadienyl ring. Preference is given to -Z-A and the aryl substituent being located in the 1,3 positions relative to one another on the cyclopentadienyl ring.

As in the cases of the metallocenes, the monocyclopentadienyl complexes of the present invention can be chiral. Thus, either one of the substituents $R^{1A}$-$R^{4A}$ on the cyclopentadienyl skeleton can bear one or more chiral centers or else the cyclopentadienyl system Cp can itself be enantiotopic, so that the chirality is induced only when it is bound to the transition metal M (for the conventions regarding chirality in cyclopentadienyl compounds, see R. Halterman, Chem. Rev. 92, (1992), 965-994).

The bridge Z between the cyclopentadienyl system Cp and the uncharged donor A is an organic divalent bridge (k=1), preferably consisting of carbon- and/or silicon- and/or boron-containing bridge members. Changing the length of the link between the cyclopentadienyl system and A enables the activity of the catalyst to be influenced.

Possible carboorganic substituents $R^{6A}$-$R^{11A}$ on the link Z are, for example the following: hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond can be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, or arylalkyl which may be substituted by further alkyl groups, e.g. benzyl, o-, m-, p-methylbenzyl, 1- or 2-ethylphenyl, where two radicals $R^{6A}$ to $R^{11A}$ may also be joined to form a 5- or 6-membered ring, for example cyclohexane, and the organic radicals-$R^{6A}$-$R^{11A}$ may also be substituted by halogens such as fluorine, chlorine or bromine, for example pentafluorophenyl or bis-3,5-trifluoromethylphen-1-yl, and alkyl or aryl.

In organosilicon substituents $SiR^{12A}_3$, possible radicals $R^{12A}$ are the same radicals mentioned in more detail above for $R^{6A}$-$R^{11A}$, where two $R^{12A}$ may also be joined to form a 5- or 6-membered ring, e.g. trimethylsilyl, triethylsilyl, butyldimethylsilyl, tributylsilyl, tri-tert-butylsilyl, triallylsilyl, triphenylsilyl or dimethylphenylsilyl. Preferred radicals $R^{12A}$ are methyl, ethyl, n-propyl, n-butyl, isobutyl, tert-butyl, n-pentyl, n-hexyl, n-heptyl, n-octyl, benzyl, phenyl, ortho-dialkyl- or -dichloro-substituted phenyls, trialkyl- or trichloro-substituted phenyls, naphthyl, biphenyl and anthranyl.

Particularly preferred substituents $R^{6A}$ to $R^{11A}$ are hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, or arylalkyl which may be substituted by further alkyl groups, e.g. benzyl, o-, m-, p-methylbenzyl, 1- or 2-ethylphenyl, where two radicals $R^{6A}$ to $R^{11A}$ may also be joined to form a 5- or 6-membered ring, for example cyclohexane, and the organic radicals $R^{6A}$-$R^{11A}$ may also be substituted by halogens such as fluorine, chlorine or bromine, in particular fluorine, for example pentafluorophenyl or bis-3,5-trifluoromethylphen-1-yl, and alkyl or aryl. Particular preference is given to methyl, ethyl, 1-propyl, 2-isopropyl, 1-butyl, 2-tert-butyl, phenyl and pentafluorophenyl.

Z is preferably a —$CR^{6A}R^{7A}$—, —$SiR^{6A}R^{7A}$— group, in particular —$Si(CH_3)_2$—, —$CR^{6A}R^{7A}CR^{8A}R^{9A}$—, —$SiR^{6A}R^{7A}CR^{8A}R^{9A}$— or substituted or unsubstituted 1,2-phenylene and in particular —$CR^{6A}R^{7A}$—. Here, the preferred embodiments of the substituents $R^{6A}$ to $R^{11A}$ described above are likewise preferred embodiments. —$CR^{6A}R^{7A}$— is preferably a —$CHR^{6A}$—, —$CH_2$— or —$C(CH_3)_2$— group. The group —$SiR^{6A}R^{7A}$— in -L$^{1A}R^{6A}R^{7A}CR^{8A}R^{9A}$— can be bound to the cyclopentadienyl system or to A. This group —$SiR^{6A}R^{7A}$— or its preferred embodiments is preferably bound to Cp.

k is 0 or 1, and is in particular equal to 1 or when A is an unsubstituted, substituted or fused, heterocyclic ring system can also be 0.

A is an uncharged donor containing an atom of group 15 or 16 of the Periodic Table or a carbene, preferably one or more atoms selected from the group consisting of oxygen, sulfur, nitrogen and phosphorus, preferably nitrogen and phosphorus. The donor function in A can be bound intermolecularly or intramolecularly to the metal MA. The donor in A is preferably bound intramolecularly to M. Possible donors are uncharged functional groups containing an element of group 15 or 16 of the Periodic Table, e.g. amine, imine, carboxamide, carboxylic ester, ketone (oxo), ether, thioketone, phosphine, phosphite, phosphine oxide, sulfonyl, sulfonamide, carbenes such as N-substituted imidazol-2-ylidene or unsubstituted, substituted or fused, heterocyclic ring systems. The synthesis of the bond from A to the cyclopentadienyl radical and Z can be carried out, for example, by a method analogous to that of WO 00/35928. A is preferably a group selected from among —$OR^{13A}$—, —$SR^{13A}$—, —$NR^{13A}R^{14A}$—, —$PR^{13A}R^{14A}$—, —C=$NR^{13A}$— and unsubstituted, substituted or fused heteroaromatic ring systems, in particular —$NR^{13A}R^{14A}$—, —C=$NR^{13A}$— and unsubstituted, substituted or fused heteroaromatic ring systems.

$R^{13A}$ and $R^{14A}$ are each, independently of one another, hydrogen, $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may, be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl, alkylaryl which has from 1 to 10 carbon atoms in the alkyl part and 6-20 carbon atoms in the aryl part and may be substituted by further alkyl groups, e.g. benzyl, o-, m-, p-methylbenzyl, 1- or 2-ethylphenyl, or $SiR^{15A}_3$, where the organic radicals $R^{13A}$-$R^{14A}$ may also be substituted by halogens, e.g. fluorine, chlorine or bromine, or nitrogen-containing groups and further $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{15A}_3$ groups and two vicinal radicals $R^{13A}$-$R^{14A}$ may also be joined to form a five- or six-membered ring and the radicals $R^{15A}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part or two radicals $R^{15A}$ may also be joined to form a five- or six-membered ring.

$NR^{13A}R^{14A}$ is an amide substituent. It is preferably a secondary amide such as dimethylamide, N-ethylmethylamide, diethylamide, N-methylpropylamide, N-methylisopropylamide, N-ethylisopropylamide, dipropylamide, diisopropylamide, N-methylbutylamide, N-ethylbutylamide, N-methyl-tert-butylamide, N-tert-butylisopropylamide, dibutylamide, di-sec-butylamide, diisobutylamide, tert-amyl-tert-butylamide, dipentylamide, N-methylhexylamide, dihexylamide, tert-amyl-tertoctylamide, dioctylamide, bis(2-ethylhexyl) amide, didecylamide, N-methyloctadecylamide, N-methylcyclohexylamide, N-ethylcyclohexylamide, N-isopropylcyclohexylamide, N-tertbutylcyclohexylamide, dicyclohexylamide, pyrrolidine, piperidine, hexamethylenimine, decahydroquinoline, diphenylamine, N-methylanilide or N-ethylanilide.

In the imino group —C=$NR^{13A}$, $R^{13A}$ is preferably a $C_6$-$C_{20}$-aryl radical which may be substituted by further alkyl groups, e.g. phenyl, naphthyl, biphenyl, anthranyl, o-, m-, p-methylphenyl, 2,3-, 2,4-, 2,5-, or 2,6-dimethylphen-1-yl, 2,3,4-, 2,3,5-, 2,3,6-, 2,4,5-, 2,4,6- or 3,4,5-trimethylphen-1-yl. A is preferably an unsubstituted, substituted or fused heteroaromatic ring system which may comprise, apart from carbon ring atoms, heteroatoms from the group consisting of oxygen, sulfur, nitrogen and phosphorus. Examples of 5-membered heteroaryl groups which may, in addition to carbon atoms, contain from one to four nitrogen atoms or from one to three nitrogen atoms and/or one sulfur or oxygen atom as ring members are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups which can contain from one to four nitrogen atoms and/or a phosphorus atom are 2-pyridinyl, 2-phosphabenzolyl 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl or 1,2,4-triazin-6-yl. The 5-membered and 6-membered heteroaryl groups can also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl or 1-phenazyl. Naming and numbering of the heterocycles has been taken from L. Fieser and M. Fieser, Lehrbuch der organischen Chemie, 3$^{rd}$ revised edition, Verlag Chemie, Weinheim 1957.

Among these heteroaromatic systems A, particular preference is given to unsubstituted, substituted and/or fused six-membered heteroaromatics having 1, 2, 3, 4 or 5 nitrogen atoms in the heteroaromatic part, in particular substituted and unsubstituted 2-pyridyl, 2-quinolyl or 8-quinolyl.

A is therefore preferably a group of the formula (IVa) or (IVb)

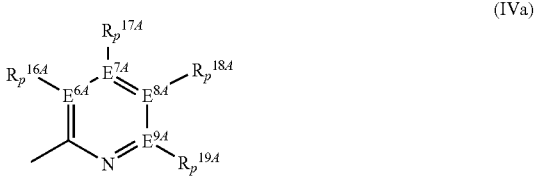

(IVa)

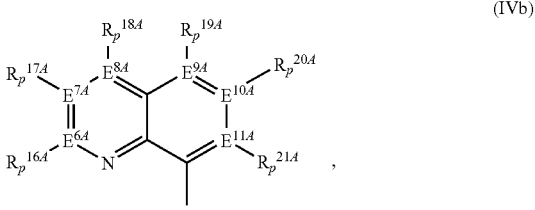

(IVb)

where
$E^{6A}$-$E^{11A}$ are each, independently of one another, carbon or nitrogen,
$R^{16A}$-$R^{21A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{22A}_3$, where the organic radicals $R^{16A}$-$R^{21A}$ may also be substituted by halogens or nitrogen and further $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{22A}_3$ groups and two vicinal radicals $R^{16A}$-$R^{21A}$ or $R^{16A}$ and Z may also be joined to form a five- or six-membered ring and
$R^{22A}$ the radicals $R^{22A}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{22A}$ may also be joined to form a five- or six-membered ring and
p is 0 when $E^{6A}$-$E^{11A}$ is nitrogen and is 1 when $E^{6A}$-$E^{11A}$ is carbon.

In particular, 0 or 1 of $E^{6A}$-$E^{11A}$ is nitrogen and the remainder are carbon. A is particularly preferably 2-pyridyl, 6-methyl-2-pyridyl, 4-methyl-2-pyridyl, 5-methyl-2-pyridyl, 5-ethyl-2-pyridyl, 4,6-dimethyl-2-pyridyl, 3-pyridazyl, 4-pyrimidyl, 6-methyl-4-pyrimidyl, 2-pyrazinyl, 6-methyl-2-pyrazinyl, 5-methyl-2-pyrazinyl, 3-methyl-2-pyrazinyl, 3-ethylpyrazinyl, 3,5,6-trimethyl-2-pyrazinyl, 2-quinolyl, 4-methyl-2-quinolyl, 6-methyl-2-quinolyl, 7-methyl-2-quinolyl, 2-quinoxalyl or 3-methyl-2-quinoxalyl.

Owing to the ease of preparation, a preferred combination of Z and A is when Z is an unsubstituted or substituted 1,2-phenylene group and A is $NR^{16A}R^{17A}$, and also the combination in which Z is —$CHR^{6A}$—, —$CH_2$—, —$C(CH_3)_2$ or —$Si(CH_3)_2$— and A is unsubstituted or substituted 2-quinolyl or un-substituted or substituted 2-pyridyl. Systems which do not have a bridge Z and in which k is 0 are also particularly simple to obtain. In this case, A is preferably a substituent of the formula (IVb) and in particular unsubstituted or substituted 8-quinolyl. The above-described preferred embodiments of the variables are also preferred in these preferred combinations.

$M^A$ is a metal selected from the group consisting of titanium in the oxidation state 3, vanadium, chromium, molybdenum and tungsten, preferably titanium in the oxidation state 3 and chromium. Particular preference is given to chromium in the oxidation states 2, 3 and 4, in particular 3. The metal complexes, in particular the chromium complexes, can be obtained in a simple manner by reacting the corresponding metal salts, e.g. metal chlorides, with the ligand anion (e.g. using a method analogous to the examples in DE 197 10615).

Among the suitable monocyclopentadienyl complexes, preference is given to those of the formula $Cp\text{-}Y_m M^A X^A_n$ (V), where the variables Cp, Y, A, m and $M^A$ are as defined above and their preferred embodiments are also preferred here and:

$X^A$ the radicals $X^A$ are each, independently of one another, fluorine, chlorine, bromine, iodine, hydrogen, $C_1$-$C_{10}$-alkyl, $C_2$-$C_{10}$-alkenyl, $C_6$-$C_{20}$-aryl, alkylaryl having 1-10 carbon atoms in the alkyl part and 6-20 carbon atoms in the aryl part, $NR^{23A}R^{24A}$, $OR^{23A}$, $SR^{23A}$, $SO_3R^{23A}$, $OC(O)R^{23A}$, CN, SCN, β-diketonate, CO, $BF_4^-$, $PF_6^-$ or bulky noncoordinating anions or two radicals $X^A$ form a substituted or unsubstituted diene ligand, in particular a 1,3-diene ligand, and the radicals $X^A$ may be joined to one another, $R^{23A}$-$R^{24A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $SiR^{25A}_3$, where the organic radicals $R^{23A}$-$R^{24A}$ may also be substituted by halogens or nitrogen- and oxygen-containing groups and two radicals $R^{23A}$-$R^{24A}$ may also be joined to form a five- or six-membered ring, $R^{25A}$ the radicals $R^{25A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two radicals $R^{25A}$ may also be joined to form a five- or six-membered ring and n is 1, 2 or 3.

The embodiments and preferred embodiments of Cp, Y, Z, A, m and $M^A$ indicated above also apply individually and in combination to these preferred monocyclopentadienyl complexes.

The ligands $X^A$ result from, for example, the choice of the metal compounds used as starting materials for the synthesis of the monocyclopentadienyl complexes, but can also be varied subsequently. Possible ligands $X^A$ are, in particular, the halogens such as fluorine, chlorine, bromine or iodine, in particular chlorine. Alkyl radicals such as methyl, ethyl, propyl, butyl, vinyl, allyl, phenyl or benzyl are also advantageous ligands $X^A$. As further ligands $X^A$, mention may be made, purely by way of example and in no way exhaustively, of trifluoroacetate, $BF_4^-$, $PF_6^-$ and weakly coordinating or non-coordinating anions (cf., for example, S. Strauss in Chem. Rev. 1993, 93, 927-942) such as $B(C_6F_5)_4^-$.

Amides, alkoxides, sulfonates, carboxylates and β-diketonates are also particularly suitable ligands $X^A$. Variation of the radicals $R^{23A}$ and $R^{24A}$ makes it possible, for example, to make fine adjustments in physical properties such as solubility. Possible carboorganic substituents $R^{23A}$-$R^{24A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N— or O-containing radicals, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6-, or 3,4,5-trimethylphenyl, 2-methoxyphenyl, 2-N,N-dimethylaminophenyl, or arylalkyl, which may be substituted by further alkyl groups, e.g. benzyl, o-, m-, p-methylbenzyl, 1- or -2-ethylphenyl, where $R^{23A}$ may also be joined to $R^{24A}$ to form a 5- or 6-membered ring and the organic radical $R^{23A}$-$R^{24A}$ may also be substituted by halogens such as fluorine, chlorine or bromine. In organosilicon substituents $SiR^{25A}_3$, the radicals $R^{25A}$ can be the same radicals described in more detail above for $R^{23A}$-$R^{24A}$, where two radicals $R^{25A}$ may also be joined to form a 5- or 6-membered ring, e.g. trimethylsilyl, triethylsilyl, butyldimethylsilyl, tributylsilyl, triallylsilyl, triphenylsilyl or dimethylphenylsilyl. Preference is given to using $C_1$-$C_{10}$-alkyl such as methyl, ethyl, n-propyl, n-butyl, tert-butyl, n-pentyl, n-hexyl, n-heptyl, n-octyl, and also vinyl, allyl, benzyl and phenyl as radicals $R^{23A}$ and $R^{24A}$. Some of these substituted ligands X are particularly preferably used because they are obtainable from cheap and readily available starting materials. Thus, a particularly preferred embodiment is that in which $X^A$ is dimethylamide, methoxide, ethoxide, isopropoxide, phenoxide, naphthoxide, triflate, p-toluolenesulfonate, acetate or acetylacetonate.

The number n of the ligands $X^A$ depends on the oxidation state of the transition metal $M^A$. The number n can therefore not be given in general terms. The oxidation state of the transition metals $M^A$ in catalytically active complexes is usually known to those skilled in the art. Chromium, molybdenum and tungsten are very probably present in the oxidation state +3, vanadium in the oxidation state +3 or +4. However, it is also possible to use complexes whose oxidation state does not correspond to that of the active catalyst. Such complexes can then be appropriately reduced or oxidized by means of suitable activators. Preference is given to using chromium complexes in the oxidation state +3 and titanium complexes in the oxidation state 3.

Preferred monocyclopentadienyl complexes A) of this type are 1-(8-quinolyl)-3-phenylcyclopentadienylchromium(III) dichloride, 1-(8-quinolyl)-3-(1-naphthyl)cyclopentadienylchromium(III) dichloride, 1-(8-quinolyl)-3-(4-trifluoromethylphenylcyclopentadienylchromium(III) dichloride, 1-(8-quinolyl)-3-(4-chlorophenyl)cyclopentadienylchromium (III) dichloride, 1-(8-quinolyl)-2-methyl-3-phenylcyclopentadienylchromium(III) dichloride, 1-(8-quinolyl)-2-methyl-3-(1-naphthyl) cyclopentadienylchromium(III) dichloride, 1-(8-quinolyl)-2-methyl-3-(4-trifluoromethylphenylcyclopentadienylchromium(III) dichloride, 1-(8-quinolyl)-2-methyl-3-(4-chlorophenyl)cyclopentadienylchromium(III) dichloride, 1-(8-quinolyl)-2-phenylindenylchromium(III) dichloride, 1-(8-quinolyl)-2-phenylbenzindenylchromium(III) dichloride, 1-(8-(2-methylquinolyl))-2-methyl-3-phenylcyclopentadienylchromium(III) dichloride, 1-(8-(2-methylquinolyl))-2-phenylindenylchromium(III) dichloride, 1-(2-pyridylmethyl)-3-phenylcyclopentadienylchromium (III) dichloride, 1-(2-pyridylmethyl)-2-methyl-3-phenylcyclopentadienylchromium(III) dichloride, 1-(2-quinolylmethyl)-3-phenylcyclopentadienylchromium dichloride, 1-(2-pyridylethyl))-3-phenylcyclopentadienylchromium dichloride, 1-(2-pyridyl-1-methylethyl)-3-phenylcyclopentadienylchromium dichloride or 1-(2-pyridyl-1-phenylmethyl)-3-phenylcyclopentadienylchromium dichloride.

The synthesis of such complexes can be carried out by methods known per se, with preference being given to reacting the appropriately substituted cyclopentadienyl anions with halides of titanium, vanadium or chromium. Examples of such preparative methods are described, inter alia, in the Journal of Organometallic Chemistry, 369 (1989), 359-370, and in EP-A-1212333.

We have also found a process for preparing cyclopentadiene systems of the formula (VIa),

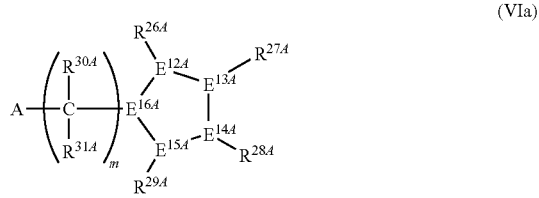

where the variables have the following meanings:

$E^{12A}$-$E^{16A}$ are each carbon, with four adjacent $E^{12A}$-$E^{16A}$ forming a conjugated diene system and the remaining $E^{12A}$-$E^{16A}$ additionally bearing a hydrogen, $R^{26A}$-$R^{29A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $NR^{32A}_2$, $N(SiR^{32A}_3)_2$, $OR^{32A}$, $OSiR^{32A}$, $BR^{32A}_2$, $SiR^{32A}_3$, where the organic radicals $R^{26A}$-$R^{26A}$ may also be substituted by halogens and two vicinal radicals $R^{26A}$-$R^{29A}$ may also be joined to form a five- or six-membered ring, and/or two vicinal radicals $R^{26A}$-$R^{29A}$ are joined to form a heterocycle which contains at least one atom from the group consisting of N, P, O or S, $R^{30A}$-$R^{31A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{32A}_3$, where the organic radicals $R^{30A}$-$R^{31A}$ may also be substituted by halogens and $R^{30A}$ or $R^{31A}$ and A may also be joined to form a five- or six-membered ring, $R^{32A}$ the radicals $R^{32A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two geminal radicals $R^{32A}$ may also be joined to form a five- or six-membered ring, m is 0, 1 or 2, A is an uncharged donor group containing one or more atoms of group 15 and/or 16 of the Periodic Table of the Elements or a carbene, preferably an unsubstituted, substituted or fused, heteroaromatic ring system, which comprises:

a) reacting an $(A\text{-}(CR^{29A}R^{30A})_m)^-$-anion with a cyclopentanedione or a silyl ether of an enolised cyclopentanedione.

Possible carboorganic substituents $R^{26A}$-$R^{31A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N— or O-containing radicals, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl or arylalkyl which may be substituted by further alkyl groups, e.g. benzyl, o-, m-, p-methylbenzyl, 1- or 2-ethylphenyl, where two vicinal radicals $R^{26A}$-$R^{29A}$ and/or $R^{30A}$ and $R^{31A}$ may also be joined to form a 5- or 6-membered ring and the organic radicals $R^{26A}$-$R^{31A}$ may also be substituted by halogens such as fluorine, chlorine or bromine. In organosilicon substituents $SiR^{32A}_3$, the radicals $R^{32A}$ can be the same radicals as have been described in more detail above for $R^{26A}$-$R^{31A}$, where two radicals $R^{32A}$ may also be joined to form a 5- or 6-membered ring, e.g. trimethylsilyl, triethylsilyl, butyldimethylsilyl, tributylsilyl, triallylsilyl, triphenylsilyl or dimethylphenylsilyl. Furthermore, $R^{26A}$-$R^{21A}$ can also be amino $NR^{32A}_2$ or $N(SiR^{32A}_3)_2$, alkoxy or aryloxy $OR^{32A}$, for example dimethylamino, N-pyrrolidinyl, picolinyl, methoxy, ethoxy or isopropoxy. Preference is given to using hydrogen and $C_1$-$C_{10}$-alkyl such as methyl, ethyl, n-propyl, n-butyl, tert-butyl, n-pentyl, n-hexyl, n-heptyl, n-octyl, phenyl or benzyl as radicals $R^{26A}$ to $R^{29A}$. Particularly useful radicals $R^{30A}$ to $R^{31A}$ are hydrogen and $C_1$-$C_{10}$-alkyl such as methyl, ethyl, n-propyl, n-butyl, tert-butyl, n-pentyl, n-hexyl, n-heptyl, n-octyl, in particular hydrogen.

The variable A and its preferred embodiments are the same as described further above.

Substituted and unsubstituted 1,2-cyclopentadiones and 1,3-cyclopentadiones have been known for a long time and are commercially available. The corresponding silyl ethers of the enolized 1,2- or 1,3-cyclopentadiones can be prepared, for example, by silylation of 1,2- or 1,3-cyclopentadiones by means of trialkylsilyl halides or triflates in the presence of catalytic amounts of base (cf. S. Torckleson et al., Synthesis 1976, 11, 722-724).

The $(A\text{-}(CR^{30A}R^{31A})_m)^-$-anion is an $A^-$-anion when m is 0, in which case the negative charge is located on A. When m is 1, it is an $(A\text{-}CR^{30A}R^{31A})^-$-anion in which the negative charge is located on the C atom bearing $R^{30A}$ and $R^{31A}$. When m is 2, the $(A\text{-}(CR^{30A}R^{31A})_m)^-$-anion is an $(A\text{-}CR^{30A}R^{31A}\text{—}CR^{30A}R^{31A})^-$-anion in which the negative charge is located on the carbon atom which bears $R^{30A}$ and $R^{31A}$ and is not bound directly to A. The variables and their preferred embodiments for A, $R^{30A}$, $R^{31A}$ and m in these anions are the same as those described above for the cyclopentadiene system (VI). The cation associated with the $(A\text{-}(CR^{30A}R^{31A})_m)^-$-anion is generally a metal of group 1 or 2 of the Periodic Table of the Elements which may bear further ligands. Particular preference is given to lithium, sodium or potassium cations which may also bear uncharged ligands such as amines or ethers and the magnesium monochloride or magnesium monobromide cation, which may likewise bear further uncharged ligands.

The negative charge on the anion $A^-$ is preferably located on a carbon of $A^-$ which is adjacent to a heteroatom of $A^-$, in particular a nitrogen atom if such an atom is present in $A^-$.

The $A^-$ anion is usually obtained by metal-halogen exchange of A-halogen with an alkyl metal compound containing $C_1$-$C_{10}$-alkyls, in particular $C_4$-alkyls, such as n-butyl and tert-butyl, and a metal of group 1 or 2, in particular lithium, magnesium monochloride or magnesium monobromide cations. Particularly useful alkyl metal compounds are, for example, lithium alkyls, magnesium alkyls, alkylmagnesium halides or mixtures thereof, in particular n-butyllithium and tertbutyllithium. The molar ratio of alkyl metal compound to A-halogen is usually in the range from 0.4:1 to 100:1, preferably in the range from 0.9:1 to 10:1 and particularly preferably from 0.95:1 to 1.1:1. Examples of such reactions are described by, inter alia, Furukawa et al. in Tet. Lett. 28 (1987), 5845.

The $(A-CR^{30A}R^{31A})^-$-anion is usually obtained by deprotonation of $A-CR^{30A}R^{31A}H$. Strong bases such as lithium alkyls, sodium hydride, sodium amides, sodium alkoxides, sodium alkyls, potassium hydride, potassium amides, potassium alkoxides, potassium alkyls, magnesium alkyls, alkylmagnesium halides or mixtures thereof can be used for this purpose. The molar ratio of base to $A-CR^{30A}R^{31A}H$ is usually in the range from 0.4:1 to 100:1, preferably in the range from 0.9:1 to 10:1 and particularly preferably from 0.95:1 to 1.1:1. Examples of such deprotonations are described in L. Brandsma, Preparative polar organometallic chemistry 2, pp. 133-142.

The $(A-CR^{30A}R^{31A}-CR^{30A}R^{31A})^-$-anion can, for example, be prepared by reacting the corresponding halide $A-CR^{30A}R^{31A}-(CR^{30A}R^{31A})$-halogen with metallic magnesium. Examples of analogous reactions, which are also referred to as Grignard Reactions, are described, for example, in Organikum, 18$^{th}$ edition, 1990, p. 499.

The reaction conditions for these reactions are described below.

The reaction product formed in the reaction with the cyclopentadione in step a) is a cyclopentenone-oxy compound which can be worked up in an aqueous medium to form the corresponding alcohol or can, for example, be reacted under acidic conditions to form the corresponding $(A-(CR^{30A}R^{31A})_m)^-$-substituted cyclopentenone. The reaction product formed by reaction with a silyl ether of an enolized cyclopentadione in step a) is a cyclopentenoxide silyl ether. Aqueous work-up and dewatering likewise leads to the corresponding $(A-(CR^{30A}R^{31A})_m)^-$-substituted cyclopentenone. The further reaction to the cyclopentadiene system (VI) is carried out in a customary fashion by alkylation, arylation or hydride addition onto the cyclopentenone, which is then formed after aqueous work-up and dewatering.

Preference is given to a process for preparing cyclopentadiene systems of the formula (VIb),

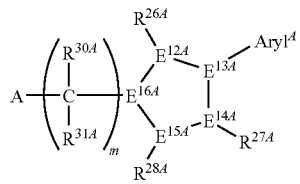

(VIb)

where the variables have the following meanings:

$E^{12A}$-$E^{16A}$ are each carbon, with four adjacent $E^{12A}$-$E^{16A}$ forming a conjugated diene system and the remaining $E^{12A}$-$E^{16A}$ additionally bearing a hydrogen, $R^{26A}$-$R^{28A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part, $SiR^{32A}_3$, where the organic radicals $R^{26A}$-$R^{25A}$ may also be substituted by halogens and two vicinal radicals $R^{27A}$-$R^{28A}$ may also be joined to form a five- or six-membered ring, and/or two vicinal radicals $R^{27A}$-$R^{28A}$ are joined to form a heterocycle which contains at least one atom from the group consisting of N, P, O or S, $R^{30A}$-$R^{31A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{32A}_3$, where the organic radicals $R^{30A}$-$R^{31A}$ may also be substituted by halogens and $R^{30A}$ or $R^{31A}$ and A may also be joined to form a five- or six-membered ring, $R^{32A}$ the radicals $R^{32A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two geminal radicals $R^{32A}$ may also be joined to form a five- or six-membered ring, Aryl$^A$ is $C_6$-$C_{22}$-aryl, for example phenyl, naphthyl, biphenyl, anthracenyl or phenanthrenyl, which may also be substituted by N—, P—, O— or S-containing substituents, $C_1$-$C_{22}$-alkyl, $C_2$-$C_{22}$-alkenyl, halogens or haloalkyls or haloaryls having 1-10 carbon atoms and m is 0 or 1, A is an unsubstituted, substituted or fused, heteroaromatic ring system, which comprises a) reacting an $(A-(CR^{30A}R^{31A})_m)^-$-anion with a cyclopentenone system of the formula (VII)

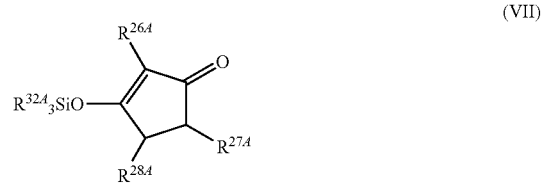

(VII)

where the variables are as defined above, to form a cyclopentenone of the formula (VIII)

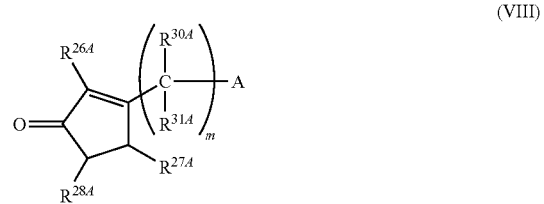

(VIII)

where the variables are as defined above. Furthermore, we have found intermediates of the formula (VIII) and cyclopentadienyl systems of the formula (VI).

Possible carboorganic substituents $R^{26A}$-$R^{31A}$ are, for example, the following: $C_1$-$C_{20}$-alkyl which may be linear or branched, e.g. methyl, ethyl, n-propyl, isopropyl, n-butyl, isobutyl, tert-butyl, n-pentyl, n-hexyl, n-heptyl, n-octyl, n-nonyl, n-decyl or n-dodecyl, 5- to 7-membered cycloalkyl which may in turn bear a $C_6$-$C_{10}$-aryl group as substituent, e.g. cyclopropyl, cyclobutyl, cyclopentyl, cyclohexyl, cycloheptyl, cyclooctyl, cyclononyl or cyclododecyl, $C_2$-$C_{20}$-alkenyl which may be linear, cyclic or branched and in which the double bond may be internal or terminal, e.g. vinyl, 1-allyl, 2-allyl, 3-allyl, butenyl, pentenyl, hexenyl, cyclopentenyl, cyclohexenyl, cyclooctenyl or cyclooctadienyl, $C_6$-$C_{20}$-aryl which may be substituted by further alkyl groups and/or N— or O-containing radicals, e.g. phenyl, naphthyl, biphenyl, anthranyl, o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, 2-methoxyphenyl, 2-N,N-dimethylaminophenyl or arylalkyl which may be substituted by further alkyl groups, e.g. benzyl, o-, m-, p-methylbenzyl, 1- or 2-ethylphenyl, where $R^{27A}$ may also be joined to $R^{28A}$ and/or $R^{30A}$ may be joined to $R^{31A}$ to form a 5- or 6-membered ring and the organic radicals $R^{26A}$-$R^{31A}$ may also be substituted by halogens such as fluorine, chlorine or bromine. In organosilicon substituents $SiR^{32}A_3$, the radicals $R^{32A}$ can be the same radicals as described further above for $R^{26A}$-$R^{30A}$, where two radicals $R^{32A}$ may also be joined to form a 5- or 6-membered ring, e.g. trimethylsilyl, triethylsilyl, butyldimethylsilyl, tributylsilyl, triallylsilyl, triphenylsilyl or dimethylphenylsilyl. Preference is given to using hydrogen and $C_1$-$C_{10}$-alkyl such as methyl, ethyl, n-propyl, n-butyl, tert-butyl, n-pentyl, n-hexyl, n-heptyl, n-octyl as radicals $R^{26A}$ to $R^{28A}$. Particularly useful radicals $R^{30A}$ to $R^{31A}$ are hydrogen and $C_1$-$C_{10}$-alkyl such as methyl, ethyl, n-propyl, n-butyl, tert-butyl, n-pentyl, n-hexyl, n-heptyl, n-octyl, in particular hydrogen.

$Aryl^A$ is $C_6$-$C_{22}$-aryl, for example phenyl, naphthyl, biphenyl, anthracenyl or phenanthrenyl, which may also be substituted by N—, P—, O— or S-containing substituents, $C_1$-$C_{22}$-alkyl, $C_2$-$C_{22}$-alkenyl, halogens or haloalkyls or haloaryls having 1-10 carbon atoms, for example o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, o-, m-, p-dimethylaminophenyl, o-, m-, p-methoxyphenyl, o-, m-, p-fluorophenyl, o-, m-, p-chlorophenyl, o-, m-, p-trifluoromethylphenyl, 2,3-, 2,4-, 2,5- or 2,6-difluorophenyl, 2,3-, 2,4-, 2,5- or 2,6-dichlorophenyl or 2,3-, 2,4-, 2,5- or 2,6-di(trifluoromethyl)phenyl.

A is an unsubstituted, substituted or fused heteroaromatic ring system which may contain heteroatoms from the group consisting of oxygen, sulfur, nitrogen and phosphorus in addition to carbon ring atoms. Examples of 5-membered heteroaryl groups, which may contain from one to four nitrogen atoms or from one to three nitrogen atoms and/or one sulfur or oxygen atom as ring atoms in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups which may contain from one to four nitrogen atoms and/or a phosphorus atom are 2-pyridinyl, 2-phosphaphenyl, 3-pyridazinyl, 2-pyrimidinyl, 4-pyrimidinyl, 2-pyrazinyl, 1,3,5-triazin-1-yl and 1,2,4-triazin-3-yl, 1,2,4-triazin-5-yl or 1,2,4-triazin-6-yl. The 5-membered and 6-membered heteroaryl groups may also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 1-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Naming and numbering of the heterocycles has been taken from L. Fieser and M. Fieser, Lehrbuch der organischen Chemie, $3^{rd}$ revised edition, Verlag Chemie, Weinheim 1957.

Among these heteroaromatic systems A, particular preference is given to unsubstituted, substituted and/or fused six-membered heteroaromatics having 1, 2, 3, 4 or 5 nitrogen atoms in the heteroaromatic part, in particular substituted and unsubstituted 2-pyridyl, 2-quinolyl or 8-quinolyl. A is therefore preferably a group of the formula (IV)

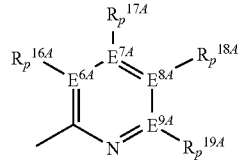

(IVa)

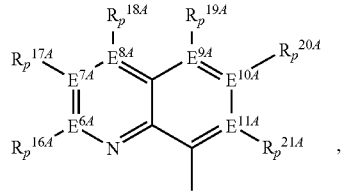

(IVb)

where $E^{6A}$-$E^{11A}$ are each, independently of one another, carbon or nitrogen, $R^{16A}$-$R^{21A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{22A}_3$, where the organic radicals $R^{16A}$-$R^{21A}$ may also be substituted by halogens or nitrogen and further $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{22A}_3$ groups and two vicinal radicals $R^{16A}$-$R^{21A}$ or $R^{16A}$ and Z may also be joined to form a five- or six-membered ring and $R^{22A}$ the radicals $R^{22A}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{22A}$ may also be joined to form a five- or six-membered ring and p is 0 when $E^{6A}$-$E^{11A}$ is nitrogen and is 1 when $E^{6A}$-$E^{11A}$ is carbon.

In particular, 0 or 1 of $E^{6A}$-$E^{11A}$ is nitrogen and the remainder carbon. A is particularly preferably 2-pyridyl, 6-methyl-2-pyridyl, 4-methyl-2-pyridyl, 5-methyl-2-pyridyl, 5-ethyl-2-pyridyl, 4,6-dimethyl-2-pyridyl, 3-pyridazyl, 4-pyrimidyl, 6-methyl-4-pyrimidyl, 2-pyrazinyl, 6-methyl-2-pyrazinyl, 5-methyl-2-pyrazinyl, 3-methyl-2-pyrazinyl, 3-ethylpyrazinyl, 3,5,6-trimethyl-2-pyrazinyl, 2-quinolyl, 4-methyl-2-quinolyl, 6-methyl-2-quinolyl, 7-methyl-2-quinolyl, 2-quinoxalyl, 3-methyl-2-quinoxalyl or 8-quinolyl.

m is 0 or 1, in particular, m is 0 when A is a donor of the formula (IVb) and is 1 when A is a donor of the formula (IVa).

Cyclopentenones of the formula (VII) have been known for a long time and can be prepared, for example, by silylation of 1,3-cyclopentadiones by means of trialkylsilyl halides or triflates in the presence of catalytic amounts of base (cf. S. Torckleson et al., Synthesis 1976, 11, 722-724).

The $(A\text{-}(CR^{30A}R^{31A})_m)^-$-anion is an $A^-$ anion when m is 0 and when m is 1 is an $(A\text{-}CR^{29A}R^{30A})^-$-anion. The variables and their preferred embodiments for A, $R^{29A}$, $R^{30A}$ and m in these anions are the same as described above for the cyclopentadiene system (VI). The cation associated with the $(A\text{-}(CR^{29A}R^{30A})_m)^-$-anion is generally a metal of group 1 or 2 of the Periodic Table of the Elements which may bear further ligands. Particular preference is given to lithium, sodium or potassium cations which may also bear uncharged ligands such as amines or ethers and the magnesium monochloride or magnesium monobromide cation which may likewise bear further uncharged ligands.

The negative charge on the anion $A^-$ is preferably located on a carbon of $A^-$ adjacent to a heteroatom of $A^-$, in particular a nitrogen atom if such an atom is present in $A^-$. $A^-$ is preferably 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl, 2-pyridinyl, 2-phosphabenzolyl, 3-pyridazinyl, 2-pyrimidinyl, 4-pyrimidinyl, 2-pyrazinyl, 1,3,5-triazin-2-yl, 1,2,4-triazin-3-yl, 1,2,4-triazin-5-yl, 1,2,4-triazin-6-yl, 2-indolyl, 7-indolyl, 2-coumaronyl, 7-coumaronyl, 2-thianaphthenyl, 7-thianaphthenyl, 3-indazolyl, 7-indazolyl, 2-benzimidazolyl or 7-benzimidazolyl, 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl or 1-phenazyl.

In the $(A\text{-}CR^{29A}R^{30A})^-$-anion, the —$CR^{29A}R^{30A}$-group bears the negative charge. This group is preferably located in the ortho position relative to a heteroatom of A, in particular a nitrogen atom if such an atom is present in A.

The $(A\text{-}(CR^{29A}R^{30A})_m)^-$ anion is preferably a group of the formula (IXa) (m=1) or of the formula (IXb) (m=0):

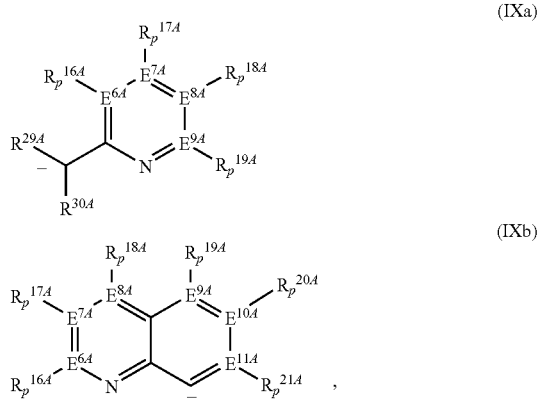

where $E^{6A}$-$E^{11A}$ are each, independently of one another, carbon or nitrogen, $R^{16A}$-$R^{21A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{22A}_3$, where the organic radicals $R^{16A}$-$R^{21A}$ may also be substituted by halogens or nitrogen and further $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{22A}_3$ groups and two vicinal radicals $R^{16A}$-$R^{21A}$ or $R^{16A}$ and Z may also be joined to form a five- or six-membered ring and $R^{22A}$ the radicals $R^{22A}$ are each, independently of one another, hydrogen, $C_1$-$C_{20}$-alkyl, $C_2$-$C_{20}$-alkenyl, $C_6$-$C_{20}$-aryl or alkylaryl having from 1 to 10 carbon atoms in the alkyl part and 6-20 carbon atoms in the aryl part and two radicals $R^{22A}$ may also be joined to form a five- or six-membered ring and $R^{29A}$-$R^{30A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or $SiR^{31A}_3$, where the organic radicals $R^{29A}$-$R^{30A}$ may also be substituted by halogens and $R^{29A}$ or $R^{30A}$ and A may also be joined to form a five- or six-membered ring, $R^{31A}$ the radicals $R^{31A}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part and two geminal radicals $R^{31A}$ may also be joined to form a five- or six-membered ring and p is 0 when $E^{6A}$-$E^{11A}$ is nitrogen and is 1 when $E^{6A}$-$E^{11A}$ is carbon.

In particular, 0 or 1 of $E^{6A}$-$E^{11A}$ is nitrogen and the remainder are carbon. Particularly preferred $A^-$-systems (IXb) are substituted and unsubstituted 8-quinolyl.

The $A^-$ anion is usually obtained by metal-halogen exchange of A-halogen with an alkyl metal compound containing $C_1$-$C_{10}$-alkyls, in particular $C_4$-alkyls, such as n-butyl and tert-butyl, and a metal of group 1 or 2, in particular lithium, magnesium monochloride or magnesium monobromide cations, Particularly useful alkyl metal compounds are, for example, lithium alkyls, magnesium alkyls, alkylmagnesium halides or mixtures thereof, in particular n-butyllithium and tertbutyllithium. The molar ratio of alkyl metal compound to A-halogen is usually in the range from 0.4:1 to 100:1, preferably in the range from 0.9:1 to 10:1 and particularly preferably from 0.95:1 to 1.1:1. Examples of such reactions are described by, inter alia, Furukawa et al. in Tet. Lett. 28 (1987), 5845.

The $(A\text{-}CR^{30A}R^{31A})^-$-anion is usually obtained by deprotonation of $A\text{-}CR^{30A}R^{31A}H$. Strong bases such as lithium alkyls, sodium hydride, sodium amides, sodium alkoxides, sodium alkyls, potassium hydride, potassium amides, potassium alkoxides, potassium alkyls, magnesium alkyls, alkylmagnesium halides or mixtures thereof can be used for this purpose. The molar ratio of base to $A\text{-}CR^{30A}R^{31A}H$ is usually in the range from 0.4:1 to 100:1, preferably in the range from 0.9:1 to 10:1 and particularly preferably from 0.95:1 to 1.1:1. Examples of such deprotonations are described in L. Brandsma, Preparative polar organometallic chemistry 2, pp. 133-142.

$A\text{-}CR^{30A}R^{31A}H$ is preferably 2-methylfuran, 2,5-dimethylfuran, 2-ethylfuran, 1,2-dimethylpyrrole, 1,2,3-trimethylpyrrole, 1,3-dimethylpyrazole, 1,2-dimethylimidazole, 1-decyl-2-methylimidazole, 1-methyl-2-undecylimidazole, 2-picoline, 2-ethylpyridine, 2-propylpyridine, 2-benzylpyridine, 2,6-lutidine, 2,4-lutidine, 2,5-lutidine, 2,3-cycloheptenopyridine, 5-ethyl-2-methylpyridine, 2,4,6-collidine, 3-methylpyridazine, 4-methylpyrimidine, 4,6-dimethylpyrimidine, 2-methylpyrazine, 2-ethylpyrazine, 2,6-dimethylpyrazine, 2,5-dimethylpyrazine, 2,3-dimethylpyrazine, 2,3-diethylpyrazine, tetrahydroquinoxaline, tetramethylpyrazine, quinaldine, 2,4-dimethylquinoline, 2,6-dimethylquinoline, 2,7-dimethylquinoline, 2-methylquinoxaline, 2,3-dimethylquinoxaline or neocuproin.

As solvents in the metal-halogen exchange step and in the deprotonation step, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The reactions can be carried out at from −100 to +160° C., in particular from −80 to 100° C. At temperatures above 40° C., preference is given to using aromatic or aliphatic solvents which contain no ethers or contain only a small proportion of ethers.

The $(A\text{-}(CR^{30A}R^{31A})_m)^-$ anion formed after metal-halogen exchange or deprotonation can be isolated or preferably reacted without further isolation with the cyclopentenone (VII). As solvents for the further reaction, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The reaction can be carried out at from −100 to +160° C., preferably from −80 to 100° C. and particularly preferably from 0 to 60° C. At temperatures above 40° C., preference is given to using aromatic or aliphatic solvents which contain no ethers or only small proportion of ethers.

The cyclopentenone of the formula (VIII) formed in step a) is then reacted further with an aryl anion $(Aryl^4)^-$ in a subsequent step b). The aryl anion has a metal cation as counteraction. This is generally a metal of group 1 or 2 of the Periodic Table of the Elements which may bear further ligands. Particular preference is given to lithium, sodium or potassium cations which may also bear uncharged ligands such as amines or ethers and the magnesium monochloride or magnesium monobromide cation which may likewise bear further uncharged ligands, in particular lithium, magnesium monochloride or magnesium monobromide cations.

$(Aryl^4)^-$ is formally a $C_6$-$C_{22}$-aryl such as phenyl, naphthyl, biphenyl, anthracenyl or phenanthrenyl which is deprotonated on the aromatic ring. The aryl may be substituted by N—, P—, O— or S-containing substituents, $C_1$-$C_{22}$-alkyl, $C_2$-$C_{22}$-alkenyl, halogens or haloalkyls or haloaryls having 1-carbon atoms, for example o-, m-, p-methylphenyl, 2,3-, 2,4-, 2,5-, or 2,6-dimethylphenyl, 2,3,4-, 2,3,5-, 2,3,6-, 2,4,5-, 2,4,6- or 3,4,5-trimethylphenyl, o-, m-, p-dimethylaminophenyl, o-, m, p-dimethylphosphinophenyl, o-, m-, p-diphenylphosphinophenyl o-, m-, p-methoxyphenyl, o-, m-, p-fluorophenyl, o-, m-, p-chlorophenyl, o-, m-, p-trifluoromethylphenyl, 2,3-, 2,4-, 2,5-, or 2,6-difluorophenyl, 2,3-, 2,4-, 2,5-, or 2,6-dichlorophenyl or 2,3-, 2,4-, 2,5- or 2,6-di(trifluoromethyl)phenyl deprotonated on the aromatic ring.

The $(Aryl^4)^-$ anion is usually obtained by metal-halogen exchange of $Aryl^4$-halogen with an alkyl metal compound containing $C_1$-$C_{10}$-alkyls, in particular $C_4$-alkyls, such as n-butyl and tert-butyl, and a metal of group 1 or 2, in particular lithium, magnesium monochloride or magnesium monobromide cations. Particularly useful alkyl metal compounds are, for example, lithium alkyls, magnesium alkyls, alkylmagnesium halides or mixtures thereof, in particular n-butyllithium and tertbutyllithium. The molar ratio of alkyl metal compound to $Aryl^4$-halogen is usually in the range from 0.4:1 to 100:1, preferably in the range from 0.9:1 to 10:1 and particularly preferably from 0.95:1 to 1.1:1. Examples of such reactions are described by, inter alia, Furukawa et al. in Tet. Lett. 28 (1987), 5845. The arylanion is associated with the metal cation from this step as cation.

Solvents and reaction temperatures suitable for this metal-halogen exchange step are the same ones as described above for the metal-halogen exchange of A-halogen. Many aryl anions are also commercially available.

The aryl anion formed after metal-halogen exchange can be isolated or preferably reacted without further isolation with the cyclopentenone (VIII). As solvents for the further reaction, it is possible to use all aprotic solvents, in particular aliphatic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. The reaction can be carried out at from −100 to +160° C., preferably from −80 to 100° C. and particularly preferably from 0 to 60° C. At temperatures above 40° C., preference is given to using aromatic or aliphatic solvents which contain no ethers or only small proportions of ethers.

The cyclopentenoxide formed by reaction of the aryl anion with the cyclopentenone (VIII) in step b) is usually protonated before dewatering. This can be achieved, for example, by means of small amounts of acid, for example HCl, or by means of aqueous work-up. The intermediate obtained in this way, a cyclopentenol, is subsequently dehydrated to form the cyclopentadiene system (VIb). This is often carried out with addition of catalytic amounts of acid such as HCl or p-toluenesulfonic acid or iodine. Dewatering can be carried out at from −10 to +160° C., preferably from 0 to 100° C. and particularly preferably from 20 to 80° C. As solvents, it is possible to use, for example, aprotic solvents, in particular alipahtic and aromatic hydrocarbons such as n-pentane, n-hexane, isohexane, n-heptane, isoheptane, decalin, benzene, toluene, ethylbenzene or xylene or ethers such as diethyl ether, dibutyl ether, tetrahydrofuran, dimethoxyethane or diethylene glycol dimethyl ether and mixtures thereof. Toluene and heptane are particularly useful. Water separators are often also used for dewatering.

The cyclopentenone (VIII) can also be reacted with an alkyl anion having from 1 to 20 carbon atoms. However, this leads, after dewatering, to a cyclopentadiene product (VI) in which aryl is replaced by alkyl.

The cyclopentadiene system (VIa) or (VIb) obtained in this way can then be deprotonated by customary methods, for example by means of potassium hydride or n-butyllithium, and reacted further with the appropriate transition metal compound, e.g. chromium trichloride tris(tetrahydrofuran), to form the corresponding monocyclopentadienyl complex (A). Furthermore, the cyclopentadiene system (Via) or (VIb) can also be reacted directly with, for example, chromium amides to form the monocyclopentadienyl complex (A) in a manner analogous to the process in EP-A-742 046.

This method of preparing the cyclopentadiene systems (VI) is particularly advantageous since it uses simple starting materials and gives good yields. The $(A\text{-}(CR^{30A}R^{31A})_m)^-$-anion is a very bulky nucleophile. It can therefore be introduced more readily by means of a Michael addition. If the aryl or alkyl is introduced first and the bulky $(A\text{-}(CR^{30A}R^{31A})_m)^-$ anion is introduced subsequently, enolizations frequently occur as secondary reactions.

The monocyclopentadienyl complexes of the present invention can be used alone or together with further components as catalyst system for olefin polymerization. We have also found catalyst systems for olefin polymerization comprising A) at least one monocyclopentadienyl complex according to the present invention,
B) optionally an organic or inorganic support,
C) optionally one or more activating compounds,
D) optionally one or more catalysts suitable for olefin polymerization and
E) optionally one or more metal compounds containing a metal of group 1, 2 or 13 of the Periodic Table.

Thus, more than one of the monocyclopentadienyl complexes of the present invention can simultaneously be brought into contact with the olefin or olefins to be polymerized. This has the advantage that a wide range of polymers can be produced in this way. For example, bimodal products can be prepared in this way.

For the monocyclopentadienyl complexes of the present invention to be able to be used in polymerization processes in the gas phase or in suspension, it is often advantageous for them to be used in the form of a solid, i.e. for them to be applied to a solid support B). Furthermore, the supported monocyclopentadienyl complexes have a high productivity. Consequently, the monocyclopentadienyl complexes of the present invention can, if desired, also be immobilized on an organic or inorganic support B) and be used in supported form in the polymerization. This enables, for example, deposits in the reactor to be avoided and the polymer morphology to be controlled. As support materials, preference is given to using silica gel, magnesium chloride, aluminum oxide, mesoporus materials, aluminosilicates, hydrotalcites and organic polymers such as polyethylene, polypropylene, polystyrene, polytetrafluoroethylene or polymers bearing polar functional groups, for example copolymers of ethene and acrylic esters, acrolein or vinyl acetate.

Particular preference is given to a catalyst system comprising a monocyclopentadienyl complex according to the present invention and at least one activating compound C) together with a support component B).

To obtain such a supported catalyst system, the unsupported catalyst system can be reacted with a support component B). The order in which support component B), monocyclopentadienyl complex A) according to the present invention and the activating compound C) is in principle immaterial. The monocyclopentadienyl complex A) of the present invention and the activating compound C) can be immobilized independently of one another or simultaneously. After the individual process steps, the solid can be washed with suitable inert solvents, e.g. aliphatic or aromatic hydrocarbons.

In a preferred method of preparing the supported catalyst system, at least one of the monocyclopentadienyl complexes of the present invention is brought into contact with at least one activating compound C) in a suitable solvent, preferably giving a soluble reaction product, an adduct or a mixture. The preparation obtained in this way is then mixed with the dehydrated or passivated support material, the solvent is removed and the resulting supported monocyclopentadienyl catalyst system is dried to ensure that all or most of the solvent is removed from the pores of the support material. The supported catalyst is obtained as a free-flowing powder. Examples of the industrial implementation of the above process are described in WO 96/00243, WO 98/40419 or WO 00/05277. In a further preferred embodiment, the activating compound C) is applied to the support component B) first and this supported compound is subsequently brought into contact with the monocyclopentadienyl complex A) of the present invention.

As support component B), preference is given to using finely divided supports which can be any organic or inorganic solid. In particular, the support component B) can be a porous support such as talc, a sheet silicate such as montmorillonite, mica, an inorganic oxide or a finely divided polymer powder (e.g. polyolefin or a polymer bearing polar functional groups).

The support materials used preferably have a specific surface area in the range from 10 to 1000 m$^2$/g, a pore volume in the range from 0.1 to 5 ml/g and a mean particle size of 1 to 500 μm. Preference is given to supports having a specific surface area in the range from 50 to 700 m$^2$/g, a pore volume in the range from 0.4 to 3.5 ml/g and a mean particle size in the range from 5 to 350 μm. Particular preference is given to supports having a specific surface area in the range from 200 to 550 m$^2$/g, a pore volume in the range from 0.5 to 3.0 ml/g and a mean particle size of from 10 to 150 μm.

The inorganic support can be subjected to a thermal treatment, e.g. to remove adsorbed water. Such a drying treatment is generally carried out at from 80 to 800° C., preferably from 100 to 300° C., with drying at from 100 to 200° C. preferably being carried out under reduced pressure and/or under a blanket of inert gas (e.g. nitrogen), or the inorganic support can be calcined at from 200 to 1000° C. to produce the desired structure of the solid and/or set the desired OH concentration on the surface. The support can also be treated chemically using customary desiccants such as metal alkyl, preferably aluminum alkyls, chlorosilanes or SiCl$_4$, or else methylaluminoxane. Appropriate treatment methods are described, for example, in WO 00/31090.

The inorganic support material can also be chemically modified. For example, treatment of silica gel with NH$_4$SiF$_6$ or other fluorinating agents leads to fluorination of the silica gel surface, or treatment of silica gels with silanes containing nitrogen-, fluorine- or sulfur-containing groups leads to correspondingly modified silica gel surfaces.

Organic support materials such as finely divided polyolefin powders (e.g. polyethylene, polypropylene or polystyrene) can also be used and are preferably likewise freed of adhering moisture, solvent residues or other impurities by appropriate purification and drying operations before use. It is also possible to use functionalized polymer supports, e.g. ones based on polystyrene, polyethylene or polypropylene, via whose functional groups, for example ammonium or hydroxy groups, at least one of the catalyst components can be fixed.

Inorganic oxides suitable as support component B) may be found among the oxides of elements of groups 2, 3, 4, 5, 13, 14, 15 and 16 of the Periodic Table of the Elements. Examples of oxides preferred as supports include silicon dioxide, aluminum oxide and mixed oxides of the elements calcium, aluminum, silicon, magnesium or titanium and also corresponding oxide mixtures. Other inorganic oxides which can be used alone or in combination with the abovementioned preferred oxidic supports are, for example, MgO, CaO, AlPO$_4$, ZrO$_2$, TiO$_2$, B$_2$O$_3$ or mixtures thereof.

As solid support materials B) for catalysts for olefin polymerization, preference is given to using silica gels since particles whose size and structure make them suitable as supports for olefin polymerization can be produced from this material. Spray-dried silica gels comprising spherical agglomerates of smaller granular particles, i.e. primary particles, have been found to be particularly useful. These silica gels can be dried and/or calcined before use.

Further preferred supports B) are hydrotalcites and calcined hydrotalcites. In mineralogy, hydrotalcite is a natural mineral having the ideal formula

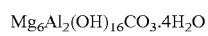

$$Mg_6Al_2(OH)_{16}CO_3.4H_2O$$

whose structure is derived from that of brucite Mg(OH)$_2$. Brucite crystallizes in a sheet structure with the metal ions in octahedral holes between two layers of close-packed hydroxyl ions, with only every second layer of the octahedral holes being occupied. In hydrotalcite, some magnesium ions are replaced by aluminum ions, as a result of which the packet of layers gains a positive charge. This is compensated by the anions which are located together with water of crystallization in the layers in between.

Such sheet structures are found not only in magnesium-aluminum hydroxides, but also generally in mixed metal hydroxides of the formula $$M(II)_{2x}^{2+} M(III)_2^{3+} (OH)_{4x+4} \cdot A_{2/n}^{n-} \cdot zH_2O$$

which have a sheet structure and in which M(II) is a divalent metal such as Mg, Zn, Cu, Ni, Co, Mn, Ca and/or Fe and M(III) is a trivalent metal such as Al, Fe, Co, Mn, La, Ce and/or Cr, x is from 0.5 to 10 in steps of 0.5, A is an interstitial anion and n is the charge on the interstitial anion which can be from 1 to 8, usually from 1 to 4, and z is an integer from 1 to 6, in particular from 2 to 4. Possible interstitial anions are organic anions such as alkoxide anions, alkyl ether sulfates, aryl ether sulfates or glycol ether sulfates, inorganic anions such as, in particular, carbonate, hydrogencarbonate, nitrate, chloride, sulfate or B(OH)$_4^-$ or polyoxo metal anions such as Mo$_7$O$_{24}^{6-}$ or V$_{10}$O$_{28}^{6-}$. However, a mixture of a plurality of such anions can also be present.

Accordingly, all such mixed metal hydroxides having a sheet structure should be regarded as hydrotalcites for the purposes of the present invention.

Calcined hydrotalcites can be prepared from hydrotalcites by calcination, i.e. heating, by means of which, inter alia, the desired hydroxyl group content can be set. In addition, the crystal structure also changes. The preparation of the calcined hydrotalcites used according to the present invention is usually carried out at temperatures above 180° C. Preference is given to calcination for from 3 to 24 hours at from 250° C. to 1000° C., in particular from 400° C. to 700° C. It is possible for air or inert gas to be passed over the solid during calcination or for a vacuum to be applied.

On heating, the natural or synthetic hydrotalcites firstly give off water, i.e. drying occurs. On further heating, the actual calcination, the metal hydroxides are converted into the metal oxides by elimination of hydroxyl groups and interstitial anions; OH groups or interstitial anions such as carbonate can also still be present in the calcined hydrotalcites. A measure of this is the loss on ignition. This is the weight loss experienced by a sample which is heated in two steps firstly for 30 minutes at 200° C. in a drying oven and then for 1 hour at 950° C. in a muffle furnace.

The calcined hydrotalcites used as component B) are thus mixed oxides of the divalent and trivalent metals M(II) and M(III), with the molar ratio of M(II) to M(III) generally being in the range from 0.5 to 10, preferably from 0.75 to 8 and in particular from 1 to 4. Furthermore, normal amounts of impurities, for example Si, Fe, Na, Ca or Ti and also chlorides and sulfates, can also be present.

Preferred calcined hydrotalcites B) are mixed oxides in which M(II) is magnesium and M(III) is aluminum. Such aluminum-magnesium mixed oxides are obtainable from Condea Chemie GmbH (now Sasol Chemie), Hamburg, under the trade name Puralox Mg.

Preference is also given to calcined hydrotalcites in which the structural transformation is complete or virtually complete. Calcination, i.e. transformation of the structure, can be confirmed, for example, by means of X-ray diffraction patterns.

The hydrotalcites, calcined hydrotalcites or silica gels employed are generally used as finely divided powders having a mean particle diameter d$_{50}$ of from 5 to 200 µm, preferably from 10 to 150 µm, particularly preferably from 15 to 100 µm and in particular from 20 to 70 µm, and usually have pore volumes of from 0.1 to 10 cm$^3$/g, preferably from 0.2 to 5 cm$^3$/g, and specific surface areas of from, 30 to 1 000 m$^2$/g, preferably from 50 to 800 m$^2$/g and in particular from 100 to 600 m$^2$/g. The monocyclopentadienyl complexes of the present invention are preferably applied in such an amount that the concentration of transition metal complexes in the finished catalyst system is from 5 to 200 µmol, preferably from 20 to 100 µmol and particularly preferably from 25 to 70 µmol per g of support B).

Some of the monocyclopentadienyl complexes of the present invention have little polymerization activity on their own and are then brought into contact with an activator, viz. the component C), to be able to display good polymerization activity. For this reason, the catalyst system optionally further comprises, as component C), one or more activating compounds, preferably at least one cation-forming compound C).

Suitable compounds C) which are able to react with the monocyclopentadienyl complex A) to convert it into a catalytically active, or more active, compound are, for example, compounds such as an aluminoxane, a strong uncharged Lewis acid, an ionic compound having a Lewis-acid cation or an ionic compound containing a Brönsted acid as cation.

As aluminoxanes, it is possible to use, for example, the compounds described in WO 00/31090. Particularly useful aluminoxanes are open-chain or cyclic aluminoxane compounds of the formula (X) or (XI)

(X)

(XI)

where R$^{1C}$-R$^{4C}$ are each, independently of one another, a C$_1$-C$_6$-alkyl group, preferably a methyl, ethyl, butyl or isobutyl group, and I is an integer from 1 to 30, preferably from 5 to 25.

A particularly useful aluminoxane compound is methylaluminoxane.

These oligomeric aluminoxane compounds are usually prepared by controlled reaction of a solution of trialkylaluminum with water. In general, the oligomeric aluminoxane compounds obtained in this way are in the form of mixtures of both linear and cyclic chain molecules of various lengths, so that I is to be regarded as a mean. The aluminoxane compounds can also be present in admixture with other metal alkyls, usually aluminum alkyls. Aluminoxane preparations suitable as component C) are commercially available.

Furthermore, modified aluminoxanes in which some of the hydrocarbon radicals have been replaced by hydrogen atoms or alkoxy, aryloxy, siloxy or amide radicals can also be used as component C) in place of the aluminoxane compounds of the formula (X) or (XI).

It has been found to be advantageous to use the monocyclopentadienyl complexes A) and the aluminoxane compounds in such amounts that the atomic ratio of aluminum from the aluminoxane compounds including any aluminum alkyl still present to the transition metal from the monocyclopentadienyl complex A) is in the range from 1:1 to 1 000:1, preferably from 10:1 to 500:1 and in particular in the range from 20:1 to 400:1.

A further class of suitable activating components C) are hydroxyaluminoxanes. These can be prepared, for example, by addition of from 0.5 to 1.2 equivalents of water, preferably from 0.8 to 1.2 equivalents of water, per equivalent of aluminum to an alkylaluminum compound, in particular triisobutylaluminum, at low temperatures, usually below 0° C. Such compounds and their use in olefin polymerization are described, for example, in WO 00/24787. The atomic ratio of aluminum from the hydroxyaluminoxane compound to the transition metal from the monocyclopentadienyl complex A) is usually in the range from 1:1 to 100:1, preferably from 10:1 to 50:1 and in particular in the range from 20:1 to 40:1. Preference is in this case given to using a monocyclopentadienyl metal dialkyl compound A).

As strong, uncharged Lewis acids, preference is given to compounds of the formula (XII)

$$M^{1C}X^{1C}X^{2C}X^{3C} \quad \text{(XII)}$$

where
$M^{1C}$ is an element of group 13 of the Periodic Table of the Elements, in particular B, Al or Ga, preferably B,
$X^{1C}$, $X^{2C}$ and $X^{3C}$ are each hydrogen, $C_1$-$C_{10}$-alkyl, $C_6$-$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryls, preferably pentafluorophenyl.

Further examples of strong, uncharged Lewis acids are given in WO 00/31090.

Compounds of this type which are particularly useful as component C) are boranes and boroxins such as trialkylborane, triarylborane or trimethylboroxin. Particular preference is given to using boranes which bear at least two perfluorinated aryl radicals. Particular preference is given to compounds of the formula (XII) in which $X^{1C}$, $X^{2C}$ and $X^{3C}$ are identical, preferably tris(pentafluorophenyl)borane.

Suitable compounds C) are preferably prepared by reaction of aluminum or boron compounds of the formula (XII) with water, alcohols, phenol derivatives, thiophenol derivatives or aniline derivatives, with halogenated and especially perfluorinated alcohols and phenols being of particular importance. Examples of particularly useful compounds are pentafluorophenol, 1,1-bis(pentafluorophenyl)methanol and 4-hydroxy-2,2',3,3',4,4',5,5',6,6'-nonafluorobiphenyl. Examples of combinations of compounds of the formula (XII) with Brönsted acids are, in particular, trimethylaluminum/pentafluorophenol, trimethylaluminum/1-bis(pentafluorophenyl)methanol, trimethylaluminum/4-hydroxy-2,2',3,3',4,4',5, 5',6,6'-nonafluorobiphenyl, triethylaluminum/ pentafluorophenol and triisobutylaluminum/ pentafluorophenol and triethylaluminum/4,4'-dihydroxy-2, 2',3,3',5,5',6,6'-octafluorobiphenyl hydrate.

In further suitable aluminum and boron compounds of the formula (XII), $X^{1C}$ is an OH group. Examples of compounds of this type are boronic acids and borinic acids, in particular borinic acids having perfluorinated aryl radicals, for example $(C_6F_5)_2BOH$.

Strong uncharged Lewis acids suitable as activating compounds C) also include the reaction products of a boronic acid with two equivalents of an aluminum trialkyl or the reaction products of an aluminum trialkyl with two equivalents of an acidic fluorinated, in particular perfluorinated, hydrocarbon compound such as pentafluorophenol or bis(pentafluorophenyl)borinic acid.

Suitable ionic compounds having Lewis acid cations include salt-like compounds of the cation of the formula (XIII)

$$[((M^{2C})^{a+})Q_1Q_2\ldots Q_z]^{d+} \quad \text{(XIII)}$$

where
$M^{2C}$ is an element of groups 1 to 16 of the Periodic Table of the Elements,
$Q_1$ to $Q_z$ are singly negatively charged groups such as $C_1$-$C_{28}$-alkyl, $C_6$-$C_{15}$-aryl, alkylaryl, arylalkyl, haloalkyl, haloaryl each having from 6 to 20 carbon atoms in the aryl radical and from 1 to 28 carbon atoms in the alkyl radical, $C_3$-$C_{10}$-cycloalkyl which may bear $C_1$-$C_{10}$-alkyl groups as substituents, halogen, $C_1$-$C_{28}$-alkoxy, $C_6$-$C_{15}$-aryloxy, silyl or mercaptyl groups,
a is an integer from 1 to 6 and
z is an integer from 0 to 5,
d corresponds to the difference a-z, but d is greater than or equal to 1.

Particularly useful cations are carbonium cations, oxonium cations and sulfonium cations and also cationic transition metal complexes. Particular mention may be made of the triphenylmethyl cation, the silver cation and the 1,1'-dimethylferrocenyl cation. They preferably have noncoordinating counterions, in particular boron compounds as are also mentioned in WO 91/09882, preferably tetrakis(pentafluorophenyl)borate.

Salts having noncoordinating anions can also be prepared by combining a boron or aluminum compound, e.g. an aluminum alkyl, with a second compound which can react to link two or more boron or aluminum atoms, e.g. water, and a third compound which forms an ionizing ionic compound with the boron or aluminum compound, e.g. triphenylchloromethane, or optionally a base, preferably an organic nitrogen-containing base, for example an amine, an aniline derivative or a nitrogen heterocycle. In addition, a fourth compound which likewise reacts with the boron or aluminum compound, e.g. pentafluorophenol, can be added.

Ionic compounds containing Brönsted acids as cations preferably likewise have noncoordinating counterions. As Brönsted acid, particular preference is given to protonated amine or aniline derivatives.

Preferred cations are N,N-dimethylanilinium, N,N-dimethylcyclohexylammonium and N,N-dimethylbenzylammonium and also derivatives of the latter two.

Compounds containing anionic boron heterocycles as are described in WO 9736937 are also suitable as component C), in particular dimethylanilinium boratabenzene or trityl boratabenzene.

Preferred ionic compounds C) contain borates which bear at least two perfluorinated aryl radicals. Particular preference is given to N,N-dimethylanilinium tetrakis(pentafluorophenyl)borate and in particular N,N-dimethylcyclohexylammonium tetrakis(pentafluorophenyl)borate, N,N-dimethylbenzylammonium tetrakis(pentafluorophenyl)borate or trityl tetrakispentafluorophenylborate.

It is also possible for two or more borate anions and/or boranes to be joined to one another or for a borate anion to be joined to a borane, as in the dianion $[(C_6F_5)_3B—C_6F_4—B(C_6F_5)_3]^{2-}$ or the anion $[(C_6F_5)_3B—CN—B(C_6F_5)_3]^-$, or the borate anion can be bound via a bridge bearing a suitable functional group to the support surface.

Further suitable activating compounds C) are listed in WO 00/31090.

The amount of strong, uncharged Lewis acids, ionic compounds having Lewis-acid cations or ionic compounds containing Brönsted acids as cations is preferably from 0.1 to 20 equivalents, more preferably from 1 to 10 equivalents, based on the monocyclopentadienyl complex A).

Suitable activating compounds C) also include boron-aluminum compounds such as di[bis(pentafluorophenyl) boroxy]methylalane. Examples of such boron-aluminum compounds are those disclosed in WO 99/06414.

It is also possible to use mixtures of all the abovementioned activating compounds C). Preferred mixtures comprise aluminoxanes, in particular methylaluminoxane, and an ionic compound, in particular one containing the tetrakis(pentafluorophenyl)borate anion, and/or a strong uncharged Lewis acid, in particular tris(pentafluorophenyl)borane.

Both the monocyclopentadienyl complexes A) and the activating compounds C) are preferably used in a solvent, preferably an aromatic hydrocarbon having from 6 to 20 carbon atoms, in particular xylenes, toluene, pentane, hexane, heptane or a mixture thereof.

A further possibility is to use an activating compound C) which can simultaneously be employed as support B). Such systems are obtained, for example, from an inorganic oxide by treatment with zirconium alkoxide and subsequent chlorination, for example by means of carbon tetrachloride. The preparation of such systems is described, for example, in WO 01/41920.

A likewise broad product spectrum can be achieved by use of the monocyclopentadienyl complexes A) of the present invention in combination with at least one further catalyst D) which is suitable for the polymerization of olefins. It is therefore possible to use one or more catalysts suitable for olefin polymerization as optional component D) in the catalyst system. Possible catalysts D) are, in particular, classical Ziegler-Natta catalysts based on titanium and classical Phillips catalysts based on chromium oxides.

Possible components D) are in principle all compounds of transition metals of groups 3 to 12 of the Periodic Table or the lanthanides which contain organic groups and preferably form active catalysts for olefin polymerization after reaction with the components C) in the presence of A) and optionally B) and/or E). These are usually compounds in which at least one monodentate or polydentate ligand is bound to the central atom via a sigma or pi bond. Possible ligands include both ligands containing cyclopentadienyl groups and ligands which are free of cyclopentadienyl groups. A large number of such compounds B) suitable for olefin polymerization are described in Chem. Rev. 2000, Vol, 100, No. 4. Furthermore, multinuclear cyclopentadienyl complexes are also suitable for olefin polymerization.

Particularly well-suited components D) include compounds having at least one cyclopentadienyl ligand, which are generally referred to as metallocene-complexes. Particularly useful metallocene complexes are those of the formula (XIV)

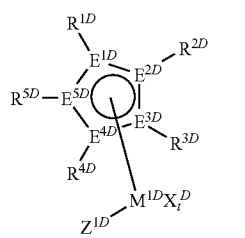

(XIV)

where the substituents and indices have the following meanings:

$M^{1D}$ is titanium, zirconium, hafnium, vanadium, niobium, tantalum, chromium, molybdenum or tungsten, or an element of group 3 of the Periodic Table and the lanthanides, $X^D$ is fluorine, chlorine, bromine, iodine, hydrogen, $C_1$-$C_{10}$-alkyl, $C_2$-$C_{10}$-alkenyl, $C_6$-$C_{15}$-aryl, alkylaryl having from 1 to 10 carbon atoms in the alkyl part and from 6 to 20 carbon atoms in the aryl part, —$OR^{6D}$ or —$NR^{6D}R^{7D}$, or two radicals $X^D$ form a substituted or unsubstituted diene ligand, in particular a 1,3-diene ligand, and the radicals $X^D$ are identical or different and may be joined to one another, $E^{1D}$-$E^{5D}$ are each carbon or not more than one $E^{1D}$ to $E^{5D}$ is phosphorus or nitrogen, preferably carbon, t is 1, 2 or 3 and is such that, depending on the valence of $M^{1D}$, the metallocene complex of the formula (XIV) is uncharged, where $R^{6D}$ and $R^{7D}$ are each $C_1$-$C_{10}$-alkyl, $C_6$-$C_{15}$-aryl, alkylaryl, arylalkyl, fluoroalkyl or fluoroaryl each having from 1 to 10 carbon atoms in the alkyl radical and from 6 to 20 carbon atoms in the aryl radical and $R^{1D}$ to $R^{5D}$ are each, independently of one another, $C_1$-$C_{22}$-alkyl, 5- to 7-membered cycloalkyl or cycloalkenyl which may in turn bear $C_1$-$C_{10}$-alkyl groups as substituents, $C_2$-$C_{22}$-alkenyl, $C_6$-$C_{22}$-aryl, arylalkyl having from 1 to 16 carbon atoms in the alkyl part and from 6 to 21 carbon atoms in the aryl part, $NR^{8D}_2$, $N(SiR^{8D}_3)_2$, $OR^{8D}$, $OSiR^{8D}_3$, $SiR^{8D}_3$, where the organic radicals $R^{1D}$-$R^{5D}$ may also be substituted by halogens and/or two radicals $R^{1D}$-$R^{5D}$, in particular vicinal radicals, may also be joined to form a five- six- or seven-membered ring, and/or two vicinal radicals $R^{1D}$-$R^{5D}$ may be joined to form a five-, six- or seven-membered heterocycle which contains at least one atom from the group consisting of N, P, O and S, where $R^{8D}$ the radicals $R^{8D}$ can be identical or different and are each $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy and $Z^{1D}$ is defined as for $X^D$ or,

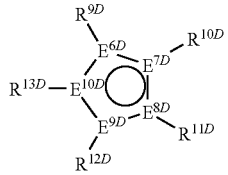

where the radicals $R^{9D}$ to $R^{13D}$ are each, independently of one another, hydrogen, $C_1$-$C_{22}$-alkyl, 5- to 7-membered cycloalkyl or cycloalkenyl which may in turn bear $C_1$-$C_{10}$-alkyl groups as substituents, $C_2$-$C_{22}$-alkenyl, $C_6$-$C_{22}$-aryl, arylalkyl having from 1 to 16 carbon atoms in the alkyl part and 6-21 carbon atoms in the aryl part, $NR^{14D}_2$, $N(SiR^{14D}_3)_2$, $OR^{14D}$, $OSiR^{14D}_3$, $SiR^{14D}_3$, where the organic radicals $R^{9D}$-$R^{13D}$ may also be substituted by halogens and/or two radicals $R^{9D}$-$R^{13D}$, in particular vicinal radicals, may also be joined to form a five-, six- or seven-membered ring, and/or two vicinal radicals $R^{9D}$-$R^{13D}$ may be joined to form a five-, six- or seven-membered heterocycle which contains at least one atom from the group consisting of N, P, O and S, where $R^{14D}$ the radicals $R^{14}$ are identical or different and are each $C_1$-$C_{10}$-alkyl, $C_3$-$C_{10}$-cycloalkyl, $C_6$-$C_{15}$-aryl, $C_1$-$C_4$-alkoxy or $C_6$-$C_{10}$-aryloxy, $E^{6D}$-$E^{10D}$ are each carbon or not more than one $E^{6D}$ to $E^{10D}$ is phosphorus or nitrogen, preferably carbon, or the radicals $R^{4D}$ and $Z^{1D}$ together form an —$R^{15D}{}_v$-$A^{1D}$- group in which $R^{15D}$

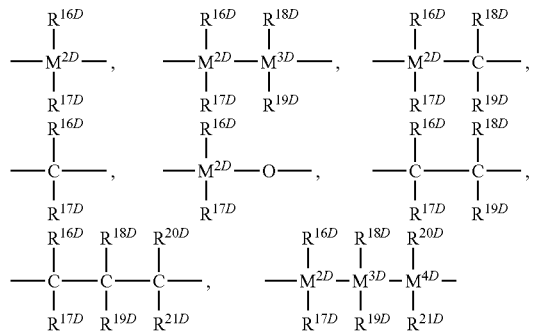

=$BR^{16D}$, =$BNR^{16D}R^{17D}$, =$AlR^{16D}$, —Ge—, —Sn—, —O—, —S—, =SO, =SO$_2$, =$NR^{16D}$, CO, $PR^{16D}$ or =$P(O)R^{16D}$, where $R^{16D}$-$R^{21D}$ are identical or different and are each a hydrogen atom, a halogen atom, a trimethylsilyl group, a $C_1$-$C_{10}$-alkyl group, a $C_1$-$C_{10}$-fluoroalkyl group, a $C_6$-$C_{10}$-fluoroaryl group, a $C_6$-$C_{10}$-aryl group, a $C_1$-$C_{10}$-alkoxy group, a $C_7$-$C_{15}$-alkylaryloxy group, a $C_2$-$C_{10}$-alkenyl group, a $C_7$-$C_{40}$-arylalkyl group, a $C_8$-$C_{40}$-arylalkenyl group or a $C_7$-$C_{40}$-alkylaryl group or two adjacent radicals together with the atoms connecting them form a saturated or unsaturated ring having from 4 to 15 carbon atoms, and $M^{2D}$-$M^{4D}$ are each silicon, germanium or tin, preferably silicon, $A^{1D}$ is —O—, —S—,

=O, =S, =$NR^{22D}$, —O—$R^{22D}$, —$NR^{22D}{}_2$, —$PR^{22D}{}_2$ or an unsubstituted, substituted or fused heterocyclic ring system, where $R^{22D}$ the radicals $R^{22D}$ are each, independently of one another, $C_1$-$C_{10}$-alkyl, $C_6$-$C_{15}$-aryl, $C_3$-$C_{10}$-cycloalkyl, $C_7$-$C_{18}$-alkylaryl or Si($R^{23D}$)$_3$, $R^{23D}$ is hydrogen, $C_1$-$C_{10}$-alkyl, $C_6$-$C_{15}$-aryl which may in turn bear $C_1$-$C_4$-alkyl groups as substituents or $C_3$-$C_{10}$-cycloalkyl, v is 1 or when $A^{1D}$ is an unsubstituted, substituted or fused heterocyclic ring system may also be 0, or the radicals $R^{4D}$ and $R^{12D}$ together form a —$R^{15D}$— group.

$A^{1D}$ together with the bridge $R^{15D}$ can, for example, form an amine, ether, thioether or phosphine. However, $A^{1D}$ may also be an unsubstituted, substituted or fused heterocyclic aromatic ring system which can contain heteroatoms from the group consisting of oxygen, sulfur, nitrogen and phosphorus in addition to carbon atoms in the ring. Examples of five-membered heteroaryl groups which can contain from one to four nitrogen atoms and/or a sulfur or oxygen atom as ring atoms in addition to carbon atoms are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups, which can contain from one to four nitrogen atoms and/or a phosphorus atom, are 2-pyridinyl, 2-phosphaphenyl, 3-pyridazinyl, 2-pyrimidinyl, 4-pyrimidinyl, 2-pyrazinyl, 1,3,5-triazin-2-yl and 1,2,4-triazin-3-yl, 1,2,4-triazin-5-yl and 1,2,4-triazin-6-yl. The 5-membered and 6-membered heteroaryl groups can also be substituted by $C_1$-$C_{10}$-alkyl, $C_6$-$C_{10}$-aryl, alkylaryl having from 1 to 10 carbon atoms in the alkyl part and 6-10 carbon atoms in the aryl part, trialkylsilyl or halogens such as fluorine, chlorine or bromine or be fused with one or more aromatics or heteroaromatics. Examples of benzo-fused 5-membered heteroaryl groups are 2-indolyl, 7-indolyl, 2-coumaronyl, 7-coumaronyl, 2-thianaphthenyl, 7-thianaphthenyl, 3-indazolyl, 7-indazolyl, 2-benzimidazolyl and 7-benzimidazolyl. Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. Naming and numbering of the heterocycles has been taken from L. Fieser and M. Fieser, Lehrbuch der organischen Chemie, 3rd revised edition, Verlag Chemie, Weinheim 1957.

It is preferred that the radicals $X^D$ in the formula (XIV) are identical, preferably fluorine, chlorine, bromine, $C_1$-$C_7$-alkyl or aralkyl, in particular chlorine, methyl or benzyl.

The synthesis of such complexes can be carried out by methods known per se, preferably by reaction of the appropriately substituted, cyclic hydrocarbon anions with halides of titanium, zirconium, hafnium or chromium.

Among the metallocene complexes of the formula (XIV), preference is given to

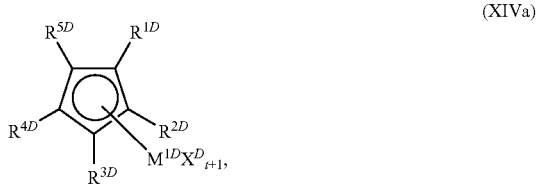

(XIVa)

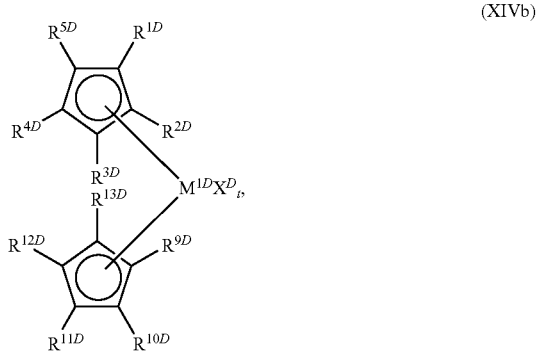

(XIVb)

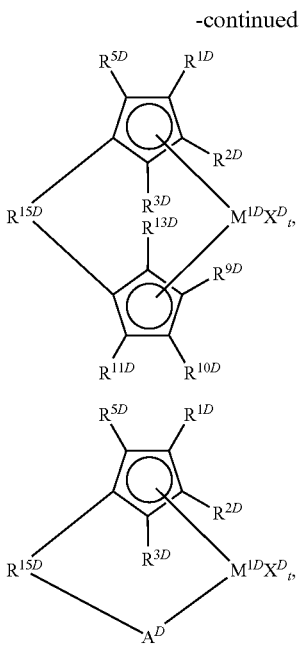

Among the compounds of the formula (XIVa), particular preference is given to those in which $M^{1D}$ is titanium, vanadium or chromium, $X^D$ is chlorine, $C_1$-$C_4$-alkyl, phenyl, alkoxy or aryloxy, t is 1 or 2 and $R^{1D}$ to $R^{5D}$ are each hydrogen, $C_1$-$C_6$-alkyl or two adjacent radicals $R^{1D}$ to $R^{5D}$ form a substituted or unsubstituted benzo group.

Among the compounds of the formula (XIVb), preference is given to those in which $M^{1D}$ is titanium, zirconium, vanadium, hafnium or chromium, $X^D$ is fluorine, chlorine, $C_1$-$C_4$-alkyl or benzyl, or two radicals $X^D$ form a substituted or unsubstituted butadiene ligand, t is 0 in the case of chromium, otherwise 1 or 2, preferably 2, $R^{1D}$ to $R^{5D}$ are each hydrogen, $C_1$-$C_8$-alkyl, $C_6$-$C_8$-aryl, $NR^{8D}_2$, $OSiR^{8D}_3$ or $Si(R^{8D})_3$ and $R^{9D}$ to $R^{13D}$ are each hydrogen, $C_1$-$C_8$-alkyl or $C_6$-$C_8$-aryl, $NR^{14D}_2$, $OSiR^{14D}_3$ or $Si(R^{14D})_3$ or two radicals $R^{1D}$ to $R^{5D}$ and/or $R^{9D}$ to $R^{13D}$ together with the $C_5$ ring form an indenyl, fluorenyl or substituted indenyl or fluorenyl system.

The compounds of the formula (XIVb) in which the cyclopentadienyl radicals are identical are particularly useful.

Examples of particularly useful compounds D) of the formula (XIVb) include: bis(cyclopentadienyl)chromium, bis (indenyl)titanium dichloride, bis(fluorenyl)titanium dichloride, bis(tetrahydroindenyl)titanium dichloride, bis (pentamethylcyclopentadienyl)titanium dichloride, bis (trimethylsilylcyclopentadienyl)titanium dichloride, bis (trimethoxysilylcyclopentadienyl)titanium dichloride, bis (isobutylcyclopentadienyl)titanium dichloride, bis(3-butenylcyclopentadienyl)titanium dichloride, bis (methylcyclopentadienyl)titanium dichloride, bis(1-,3-ditertbutylcyclopentadienyl)titanium dichloride, bis (trifluoromethylcyclopentadienyl)titanium dichloride, bis (tert-butylcyclopentadienyl)titanium dichloride, bis(n-butylcyclopentadienyl)titanium dichloride, bis (phenylcyclopentadienyl)titanium dichloride, bis(N,N-dimethylaminomethylcyclopentadienyl)titanium dichloride, bis(1,3-dimethylcyclopentadienyl)titanium dichloride, bis (1-methyl-3-n-butylcyclopentadienyl)titanium dichloride, (cyclopentadienyl)(methylcyclopentadienyl)titanium dichloride, (cyclopentadienyl)(n-butylcyclopentadienyl)titanium dichloride, (methylcyclopentadienyl)(n-butylcyclopentadienyl)titanium dichloride, (cyclopentadienyl)(1-methyl-3-butylcyclopentadienyl)titanium dichloride, bis (cyclopentadienyl)zirconium dichloride, bis (pentamethylcyclopentadienyl)zirconium dichloride, bis (methylcyclopentadienyl)zirconium dichloride, bis (ethylcyclopentadienyl)zirconium dichloride, bis(n-butylcyclopentadienyl)zirconium dichloride, bis(tert-butylcyclopentadienyl)zirconium dichloride, bis (isobutylcyclopentadienyl)zirconium dichloride, bis(3-butenylcyclopentadienyl)zirconium dichloride, bis (trifluoromethylcyclopentadienyl)zirconium dichloride, bis (phenylcyclopentadienyl)zirconium dichloride, bis(1,3-dimethylcyclopentadienyl)zirconium dichloride, bis(1-n-butyl-3-methylcyclopentadienyl)zirconium dichloride, bis (1,3-ditert-butylcyclopentadienyl)zirconium dichloride, bis (tetramethylcyclopentadienyl)zirconium dichloride, bis (indenyl)zirconium dichloride, bis(tetrahydroindenyl) zirconium dichloride, bis(fluorenyl)zirconium dichloride, (cyclopentadienyl)(methylcyclopentadienyl)zirconium dichloride, (cyclopentadienyl)(n-butylcyclopentadienyl)zirconium dichloride, (methylcyclopentadienyl)(n-butylcyclopentadienyl)zirconium dichloride, (cyclopentadienyl)(1-methyl-3-n-butylcyclopentadienyl)zirconium dichloride, bis (trimethoxysilylcyclopentadienyl)zirconium dichloride and bis(trimethylsilylcyclopentadienyl)zirconium dichloride, and also the corresponding dimethylzirconium compounds.

Particularly useful compounds of the formula (XIVc) are those in which $R^{15D}$ is

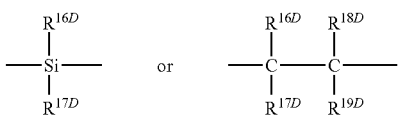

or $=BR^{16D}$ or $=BNR^{16D}R^{17D}$, $M^{1D}$ is titanium, zirconium or hafnium, in particular zirconium, and $X^D$ the radicals $X^D$ are identical or different and are each chlorine, $C_1$-$C_4$-alkyl, benzyl, phenyl or $C_7$-$C_{15}$-alkylaryloxy.

Particularly useful compounds of the formula (XVIc) are those of the formula (XVIc')

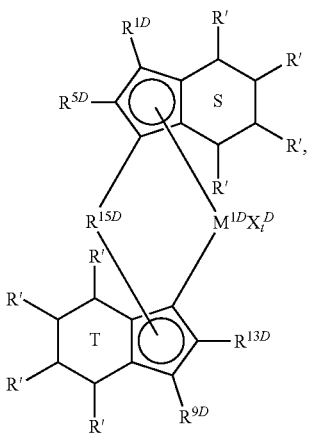

where the radicals R' are identical or different and are each hydrogen, $C_1$-$C_{10}$-alkyl or $C_3$-$C_{10}$-cycloalkyl, preferably methyl, ethyl, isopropyl or cyclohexyl, $C_6$-$C_{20}$-aryl, preferably phenyl, naphthyl or mesityl, $C_7$-$C_{40}$-arylalkyl, $C_7$-$C_{40}$-alkylaryl, preferably 4-tert-butylphenyl or 3,5-di-tert-butylphenyl, or $C_8$-$C_{40}$-arylalkenyl, $R^{5D}$ and $R^{13D}$ are identical or different and are each hydrogen, $C_1$-$C_6$-alkyl, preferably methyl, ethyl, isopropyl, n-propyl, n-butyl, n-hexyl or tert-butyl, And the rings S and T are identical or different and saturated, unsaturated or partially saturated.

The indenyl or tetrahydroindenyl ligands of the metallocenes of the formula (XIVc') are preferably substituted in the 2 position, the 2,4 positions, the 4,7 positions, the 2,4,7 positions, the 2,6 positions, the 2,4,6 positions, the 2,5,6 positions, the 2,4,5,6 positions or the 2,4,5,6,7 positions, in particular in the 2,4 positions, with the following numbering applying to the site of substitution:

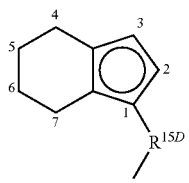

Furthermore, preference is given to using bridged bis-indenyl complexes in the rac or pseudo-rac form as component D). The term "pseudo-rac form" refers to complexes in which the two indenyl ligands are in the rac arrangement relative to one another when all other substituents of the complex are disregarded.

Further examples of particularly useful catalysts D) (XIVc) and (XIVc') include: methylenebis(cyclopentadienyl)zirconium dichloride, methylenebis(3-methylcyclopentadienyl)zirconium dichloride, methylenebis(3-n-butylcyclopentadienyl)zirconium dichloride, methylenebis(indenyl)zirconium dichloride, methylenebis(tetrahydroindenyl)zirconium dichloride, isopropylidenebis(cyclopentadienyl)zirconium dichloride, isopropylidenebis(3-trimethylsilylcyclopentadienyl)zirconium dichloride, isopropylidenebis(3-methylcyclopentadienyl)zirconium dichloride, isopropylidenebis(3-n-butylcyclopentadienyl)zirconium dichloride, isopropylidenebis(3-phenylcyclopentadienyl)zirconium dichloride, isopropylidenebis(indenyl)zirconium dichloride, isopropylidenebis(tetrahydroindenyl)zirconium dichloride, dimethylsilanediylbis(cyclopentadienyl)zirconium dichloride, dimethylsilanediylbis(indenyl)zirconium dichloride, dimethylsilanediylbis(tetrahydroindenyl)zirconium dichloride, ethylenebis(cyclopentadienyl)zirconium dichloride, ethylenebis(indenyl)zirconium dichloride, ethylenebis(tetrahydroindenyl)zirconium dichloride, tetramethylethylen-9-fluorenylcyclopentadienylzirconium dichloride, dimethylsilanediylbis(tetramethylcyclopentadienyl)zirconium dichloride, dimethylsilanediylbis(3-trimethylsilylcyclopentadienyl)zirconium dichloride, dimethylsilanediylbis(3-methylcyclopentadienyl)zirconium dichloride, dimethylsilanediylbis(3-n-butylcyclopentadienyl)zirconium dichloride dimethylsilanediylbis(3-tert-butyl-5-methylcyclopentadienyl)zirconium dichloride, dimethylsilanediylbis(3-tert-butyl-5-ethylcyclopentadienyl)zirconium dichloride, dimethylsilanediylbis(2-methylindenyl)zirconium dichloride, dimethylsilanediylbis(2-isopropylindenyl)zirconium dichloride, dimethylsilanediylbis(2-tert-butylindenyl)zirconium dichloride, diethylsilanediylbis(2-methylindenyl)zirconium dibromide, dimethylsilanediylbis(3-methyl-5-methylcyclopentadienyl)zirconium dichloride, dimethylsilanediylbis(3-ethyl-5-isopropylcyclopentadienyl)zirconium dichloride, dimethylsilanediylbis(2-ethylindenyl)zirconium dichloride, dimethylsilanediylbis(2-methyl-4,5-benzindenyl)zirconium dichloride, dimethylsilanediylbis(2-ethyl-4,5-benzindenyl)zirconium dichloride, methylphenylsilanediylbis(2-methyl-4,5-benzindenyl)zirconium dichloride, methylphenylsilanediylbis(2-ethyl-4,5-benzindenyl)zirconium dichloride, diphenylsilanediylbis(2-methyl-4,5-benzindenyl)zirconium dichloride, diphenylsilanediylbis(2-ethyl-4,5-benzindenyl)zirconium dichloride, diphenylsilanediylbis(2-methylindenyl)hafnium-dichloride, dimethylsilanediylbis(2-methyl-4-phenylindenyl)zirconium dichloride, dimethylsilanediylbis(2-ethyl-4-phenylindenyl)zirconium dichloride, dimethylsilanediylbis(2-methyl-4-(1-naphthyl)indenyl)zirconium dichloride, dimethylsilanediylbis(2-ethyl-4-(1-naphthyl)indenyl)zirconium dichloride, dimethylsilanediylbis(2-propyl-4-(1-naphthyl)indenyl)zirconium dichloride, dimethylsilanediylbis(2-1-butyl-4-(1-naphthyl)indenyl)zirconium dichloride, dimethylsilanediylbis(2-propyl-4-(9-phenanthryl)indenyl)zirconium dichloride, dimethylsilanediylbis(2-methyl-4-isopropylindenyl)zirconium dichloride, dimethylsilanediylbis(2,7-dimethyl-4-isopropylindenyl)zirconium dichloride, dimethylsilanediylbis(2-methyl-4,6-diisopropylindenyl)zirconium dichloride, dimethylsilanediylbis(2-methyl-4-[p-trifluoromethylphenyl]-indenyl)zirconium dichloride, dimethylsilanediylbis(2-methyl-4-[3',5'-dimethylphenyl]indenyl)zirconium dichloride, dimethylsilanediylbis(2-methyl-4-[4'-tert-butylphenyl]indenyl)-zirconium dichloride, diethylsilanediylbis(2-methyl-4-[4'-tert-butylphenyl]indenyl)-zirconium dichloride, dimethylsilanediylbis(2-ethyl-4-[4'-tert-butylphenyl]indenyl)-zirconium dichloride, dimethylsilanediylbis(2-propyl-4-[4'-tert-butylphenyl]indenyl)-zirconium dichloride, dimethylsilanediylbis(2-isopropyl-4-[4'-tert-butylphenyl]indenyl)-zirconium dichloride, dimethylsilanediylbis(2-n-butyl-4-[4'-tert-butylphenyl]indenyl)-zirconium dichloride, dimethylsilanediylbis(2-hexyl-4-[4'-tert-butylphenyl]indenyl)-zirconium dichloride, dimethylsilanediyl(2-isopropyl-4-phenylindenyl)(2-methyl-4-phenylindenyl)zirconium dichloride, dimethylsilanediyl(2-isopropyl-4-(1-naphthyl)indenyl)-(2-methyl-4-(1-naphthyl)indenyl)zirconium dichloride, dimethylsilanediyl(2-isopropyl-4-[4'-tert-butylphenyl]indenyl)-(2-methyl-4-[4'-tert-butylphenyl]indenyl)zirconium dichloride, dimethylsilanediyl(2-isopropyl-4-[4'-tert-butylphenyl]indenyl)-(2-ethyl-4-[4'-tert-butylphenyl]indenyl)zirconium dichloride, dimethylsilanediyl(2-isopropyl-4-[4'-tert-butylphenyl]indenyl)-(2-methyl-4-[3',5'-bis-tert-butylphenyl]indenyl)zirconium dichloride, dimethylsilanediyl(2-isopropyl-4-[4'-tert-butylphenyl]indenyl)-(2-methyl-4-[1'-naphthyl]indenyl)zirconium dichloride and ethylene(2-isopropyl-4-[4'-tert-butylphenyl]indenyl)-(2-methyl-4-[4'-tert-butylphenyl]indenyl)zirconium dichloride, and also the corresponding dimethylzirconium, monochloromono(alkylaryloxy)zirconium and di(alkylaryloxy)zirconium compounds. The complexes are preferably used in the rac form.

Such complexes can be synthesized by methods known per se, preferably by reacting the appropriately substituted, cyclic hydrocarbon anions with halides of titanium, zirconium, hafnium, vanadium, niobium, tantalum or chromium.

Examples of appropriate preparative methods are described, inter alia, in the Journal of Organometallic Chemistry, 369 (1989), 359-370.

Particularly useful compounds of the formula (XIVd) are those in which $M^{1D}$ is titanium or zirconium, in particular titanium, and
$X^D$ is chlorine, $C_1$-$C_4$-alkyl or phenyl or two radicals $X^D$ form a substituted or unsubstituted butadiene ligand,
$R^{15D}$

or $=BR^{16D}$ or $=BNR^{16D}R^{17D}$
$A^{1D}$ is

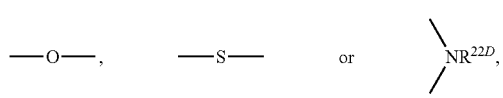

t is 1 or 2, preferably 2,
$R^{1D}$ to $R^{3D}$ and $R^{5D}$ are each hydrogen, $C_1$-$C_{10}$-alkyl, preferably methyl, $C_3$-$C_{10}$-cycloalkyl, $C_6$-$C_{15}$-aryl, $NR^{8D}{}_2$ or $Si(R^{8D})_3$, or two adjacent radicals form a cyclic group having from 4 to 12 carbon atoms, with particular preference being given to all $R^{1D}$ to $R^{3D}$ and $R^{5D}$ being methyl.

Particularly useful complexes D) of the formula (XIVd) are dimethylsilanediyl(tetramethylcyclopentadienyl)(phenylamino)titanium dichloride, dimethylsilanediyl(tetramethylcyclopentadienyl)(benzylamino)titanium dichloride, dimethylsilanediyl(tetramethylcyclopentadienyl)(tert-butylamino)titanium dichloride, dimethylsilanediyl(tetramethylcyclopentadienyl)(adamantyl)titanium dichloride and dimethylsilanediyl(indenyl)(tert-butylamino)titanium dichloride.

Another group of compounds of the formula (XIVd) which are particularly useful are those in which
$M^{1D}$ is titanium, vanadium or chromium, preferably in the oxidation state III, and
$X^D$ is chlorine, $C_1$-$C_4$-alkyl or phenyl or two radicals $X^D$ form a substituted or unsubstituted butadiene ligand,
$R^{15D}$ is

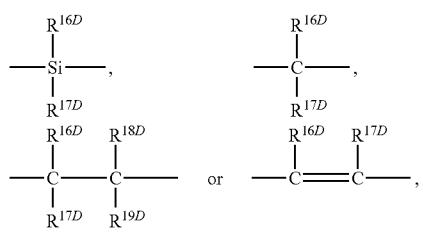

$A^{1D}$ is $-O-R^{22D}$, $-NR^{22D}{}_2$, $-PR^{22D}{}_2$ or an unsubstituted, substituted or fused, heterocyclic, in particular heteroaromatic, ring system,
v is 1 or when $A^{1D}$ is an unsubstituted, substituted or fused, heterocyclic ring system may be 0 or 1 and
$R^{1D}$ to $R^{3D}$ and $R^{5D}$ are each hydrogen, $C_1$-$C_{10}$-alkyl, $C_3$-$C_{10}$-cycloalkyl, $C_6$-$C_{15}$-aryl or $Si(R^{8D})_3$, or two adjacent radicals form a cyclic group having from 4 to 12 carbon atoms.

In a preferred embodiment, $A^{1D}$ is an unsubstituted, substituted or fused, heteroaromatic ring system and $M^{1D}$ is chromium. Very particular preference is given to $A^{1D}$ being an unsubstituted or substituted, e.g. alkyl-substituted, in particular substituted or unsubstituted quinolyl or pyridyl bound in position 8 or 2, e.g. 8-quinolyl, 8-(2-methylquinolyl), 8-(2,3,4-trimethylquinolyl), 8-(2,3,4,5,6,7-hexamethylquinolyl), v being 0 and $M^{1D}$ being chromium. Preferred catalysts D) of this type are 1-(8-quinolyl)-2-methyl-4-methylcyclopentadienylchromium(III) dichloride, 1-(8-quinolyl)-3-isopropyl-5-methylcyclopentadienylchromium(III) dichloride, 1-(8-quinolyl)-3-tert-butyl-5-methylcyclopentadienylchromium (III) dichloride, 1-(8-quinolyl)-2,3,4,5-tetramethylcyclopentadienylchromium(III) dichloride, 1-(8-quinolyl)tetrahydroindenylchromium(III) dichloride, 1-(8-quinolyl)indenylchromium(III) dichloride, 1-(8-quinolyl)-2-methylindenylchromium(III) dichloride, 1-(8-quinolyl)-2-isopropylindenylchromium(III) dichloride, 1-(8-quinolyl)-2-ethylindenylchromium(III) dichloride, 1-(8-quinolyl)-2-tert-butylindenylchromium(III) dichloride, 1-(8-quinolyl)benzindenylchromium(III) dichloride, 1-(8-quinolyl)-2-methylbenzindenylchromium(III) dichloride, 1-(8-(2-methylquinolyl))-2-methyl-4-methylcyclopentadienylchromium(III) dichloride, 1-(8-(2-methylquinolyl))-2,3,4,5-tetramethylcyclopentadienylchromium(III) dichloride, 1-(8-(2-methylquinolyl))tetrahydroindenylchromium(III) dichloride, 1-(8-(2-methylquinolyl))indenylchromium(III) dichloride, 1-(8-(2-methylquinolyl))-2-methylindenylchromium(III) dichloride, 1-(8-(2-methylquinolyl))-2-isopropylindenylchromium(III) dichloride, 1-(8-(2-methylquinolyl))-2-ethylindenylchromium(III) dichloride, 1-(8-(2-methylquinolyl))-2-tert-butylindenylchromium(III) dichloride, 1-(8-(2-methylquinolyl))benzindenylchromium(III) dichloride, 1-(2-pyridylmethyl)indenylchromium(III) dichloride or 1-(8-(2-methylquinolyl))-2-methylbenzindenylchromium(III) dichloride.

Furthermore, owing to the ease of preparation, preference is given to compounds in which $R^{15D}$ is CH=CH or 1,2-phenylene and $A^{1D}$ is $NR^{22D}{}_2$, and compounds in which $R^{15D}$ is $CH_2$, $C(CH_3)_2$ or $Si(CH_3)_2$ and $A^{1D}$ is unsubstituted or substituted 2- or 8-quinolyl or unsubstituted or substituted 2-pyridyl.

The preparation of such functional cyclopentadienyl ligands has been known for a long time. Various synthetic routes to these complexing ligands are described, for example, by M. Enders et al. in Chem. Ber. (1996), 129, 459-463, or P. Jutzi and U. Siemeling in J. Orgmet. Chem. (1995), 500, 175-185.

The metal complexes, in particular the chromium complexes, can be obtained in a simple manner by reacting the appropriate metal salts, e.g. metal chlorides, with the ligand anion (e.g. using methods analogous to the examples in DE-A-19710615).

Further suitable catalysts D) include metallocenes having at least one ligand which is formed from a cyclopentadienyl or heterocyclopentadienyl and a fused-on heterocycle, with the heterocycles preferably being aromatic and containing nitrogen and/or sulfur. Such compounds are described, for example, in WO 98/22486. These are in particular dimethylsilanediyl(2-methyl-4-phenylindenyl)(2,5-dimethyl-N-phenyl-4-azapentalene)zirconium dichloride, dimethylsilanediylbis(2-methyl-4-phenyl-4-hydroazulenyl)zirconium dichloride, dimethylsilanediylbis(2-ethyl-4-phenyl-4-hydroazulenyl)zirconium dichloride, bis(2,5-dimethyl-n-phenyl-4-azapentalene)zirconium dichloride or (indenyl)(2,5-dimethyl-N-phenyl-4-azapentalene)zirconium dichloride.

Further-suitable catalysts D) are systems in which a metallocene compound is combined with, for example, an inorganic oxide which has been treated with zirconium alkoxide and subsequently chlorinated, for example by means of carbon tetrachloride. The preparation of such systems is described, for example, in WO 01/41920.

Other suitable catalysts D) include imidochromium compounds in which chromium bears at least one imido group as structural feature. These compounds and their preparation are described, for example, in WO 01/09148.

Further suitable components D) include transition metal complexes with a tridentate macrocyclic ligand, in particular substituted and unsubstituted 1,3,5-triazacyclohexanes and 1,4,7-triazacyclononanes. In the case of this type of catalyst, preference is likewise given to chromium complexes. Preferred catalysts of this type are [1,3,5-tri(methyl)-1,3,5-triazacyclohexane]chromium trichloride, [1,3,5-tri(ethyl)-1,3,5-triazacyclohexane]chromium trichloride, [1,3,5-tri(octyl)-1,3,5-triazacyclohexane]chromium trichloride, [1,3,5-tri(dodecyl)-1,3,5-triazacyclohexane]chromium trichloride and [1,3,5-tri(benzyl)-1,3,5-triazacyclohexane]chromium trichloride.

Further suitable catalysts D) are, for example, transition metal complexes with at least one ligand of the formulae XV to XIX,

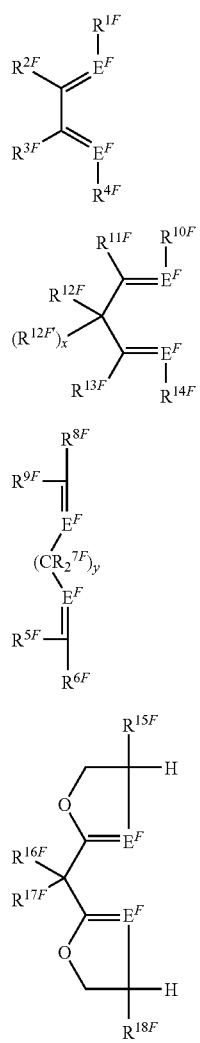

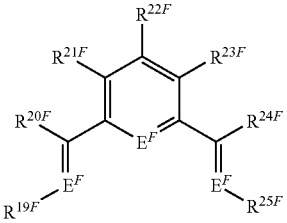

where the transition metal is selected from among the elements Ti, Zr, Hf, Sc, V, Nb, Ta, Cr, Mo, W, Fe, Co, Ni, Pd, Pt and the elements of the rare earth metals. Preference is given to compounds having nickel, iron, cobalt or palladium as central metal.

$E^F$ is an element of group 15 of the Periodic Table of the Elements, preferably N or P, with particular preference being given to N. The two or three atoms $E^F$ in a molecule can be identical or different.

The radicals $R^{1F}$ to $R^{25F}$, which may be identical or different within a ligand system XV to XIX, are as follows:

$R^{1F}$ and $R^{4F}$ are each, independently of one another, a hydrocarbon radical or a substituted hydrocarbon radical, preferably a hydrocarbon radical in which the carbon atom adjacent to the element $E^F$ is bound to at least two carbon atoms, $R^{2F}$ and $R^{3F}$ are each, independently of one another, hydrogen, a hydrocarbon radical or a substituted hydrocarbon radical, where $R^{2F}$ and $R^{3F}$ may together also form a ring system in which one or more heteroatoms may also be present, $R^{6F}$ and $R^{3F}$ are each, independently of one another, a hydrocarbon radical or a substituted hydrocarbon radical, $R^{5F}$ and $R^{9F}$ are each, independently of one another, hydrogen, a hydrocarbon radical or a substituted hydrocarbon radical, Where $R^{6F}$ and $R^{5F}$ or $R^{8F}$ and $R^{9F}$ may together also form a ring system, $R^{7F}$ the radicals $R^{7F}$ are each, independently of one another, hydrogen, a hydrocarbon radical or a substituted hydrocarbon radical, where two $R^{7F}$ may together also form a ring system, $R^{10F}$ and $R^{14F}$ are each, independently of one another, a hydrocarbon radical or a substituted hydrocarbon radical, $R^{11F}$, $R^{12F}$, $R^{12F}$, and $R^{13F}$ are each, independently of one another, hydrogen, a hydrocarbon radical or a substituted hydrocarbon radical, where two or more geminal or vicinal radicals $R^{11A}$, $R^{12A}$, $R^{12A'}$ and $R^{13A}$ may together also form a ring system, $R^{15F}$ and $R^{18F}$ are each, independently of one another, hydrogen, a hydrocarbon radical or a substituted hydrocarbon radical, $R^{16F}$ and $R^{17F}$ are each, independently of one another, hydrogen, a hydrocarbon radical or a substituted hydrocarbon radical, $R^{19F}$ and $R^{25F}$ are each, independently of one another, $C_2$-$C_{20}$-alkenyl, $C_6$-$C_{20}$-aryl, alkylaryl having from 1 to 10 carbon atoms in the alkyl part and 6-20 carbon atoms in the aryl part, where the organic radicals $R^{19F}$ and $R^{25F}$ may also be substituted by halogens, $R^{20F}$-$R^{24F}$ are each, independently of one another, hydrogen, $C_1$-$C_{20}$-alkyl, $C_2$-$C_{20}$-alkenyl, $C_6$-$C_{20}$-aryl, alkylaryl having from 1 to 10 carbon atoms in the alkyl part and 6-20 carbon atoms in the aryl part or SiR$^{26F}_3$, where the organic radicals R$^{20F}$-R$^{24F}$ may also be substituted by halogens and two vicinal radicals R$^{20F}$-R$^{24F}$ may also be joined to form a five- or six-membered ring and R$^{26F}$ the radicals R$^{26F}$ are each, independently of one another, hydrogen, C$_1$-C$_{20}$-alkyl, C$_2$-C$_{20}$-alkenyl, C$_6$-C$_{20}$-aryl or alkylaryl having from 1 to 10 carbon atoms in the alkyl part and 6-20 carbon atoms in the aryl part and two radicals R$^{26F}$ may also be joined to form a five- or six-membered ring, x is 0 or 1, with the complex of the formula (XVI) being negatively charged when x is 0, and y is an integer from 1 to 4, preferably 2 or 3.

Particularly useful transition metal complexes are those having Fe, Co, Ni, Pd or Pt as central metal and containing ligands of the formula (XV). Particular preference is given to diimine complexes of Ni or Pd, e.g.:

Di(2,6-di-i-propylphenyl)-2,3-dimethyldiazabutadienepalladium dichloride, di(di-i-propylphenyl)-2,3-dimethyldiazabutadienenickel dichloride, di(2,6-di-i-propylphenyl) dimethyldiazabutadienedimethylpalladium, di(2,6-di-i-propylphenyl)-2,3-dimethyldiazabutadienedimethylnickel, di(2,6-dimethylphenyl)-2,3-dimethyldiazabutadienepalladium dichloride, di(2,6-dimethylphenyl)-2,3-dimethyldiazabutadienenickel dichloride, di(2,6-dimethylphenyl)-2,3-dimethyldiazabutadienedimethylpalladium, di(2,6-dimethylphenyl)-2,3-dimethyldiazabutadienedimethylnickel, di(2-methylphenyl)-2,3-dimethyldiazabutadienepalladium dichloride, di(2-methylphenyl)-2,3-dimethyldiazabutadienenickel dichloride, di(2-methylphenyl)-2,3-dimethyldiazabutadienedimethylpalladium, di(2-methylphenyl)-2,3-dimethyldiazabutadienedimethylnickel, diphenyl-2,3-dimethyldiazabutadienepalladium dichloride, diphenyl-2,3-dimethyldiazabutadienenickel dichloride, diphenyl-2,3-dimethyldiazabutadienedimethylpalladium, diphenyl-2,3-dimethyldiazabutadienedimethylnickel, di(2,6-dimethylphenyl)azanaphthenepalladium dichloride, di(2,6-dimethylphenyl)azanaphthenenickel dichloride, di(2,6-dimethylphenyl)azanaphthenedimethylpalladium, di(2,6-dimethylphenyl)azanaphthenedimethylnickel, 1,1'-bipyridylpalladium dichloride, 1,1'-bipyridylnickel dichloride, 1,1'-bipyridyl(dimethyl)palladium, 1,1'-bipyridyl(dimethyl)nickel.

Particularly useful compounds (XIX) also include those which are described in J. Am. Chem. Soc. 120, p. 4049 ff. (1998), J. Chem. Soc., Chem. Commun. 1998, 849, and WO 98/27124. E$^F$ is preferably nitrogen and R$^{19F}$ and R$^{25F}$ in (XIX) are preferably phenyl, naphthyl, biphenyl, anthranyl, o-, m-, p-methylphenyl, 2,3-, 2,4-, 2,5- or 2,6-dimethylphenyl, -dichlorophenyl or -dibromophenyl, 2-chloro-6-methylphenyl, 2,3,4-, 2,3,5-, 2,3,6-, 2,4,5-, 2,4,6- or 3,4,5-trimethylphenyl, in particular 2,3- or 2,6-dimethylphenyl, -diisopropylphenol, -dichlorophenyl or -dibromophenyl and 2,4,6-trimethylphenyl. At the same time, R$^{20F}$ and R$^{24F}$ are preferably hydrogen, methyl, ethyl, n-propyl, isopropyl, n-butyl, tert-butyl, n-pentyl, n-hexyl, n-heptyl, n-octyl, benzyl or phenyl, in particular hydrogen or methyl. R$^{21F}$ and R$^{23F}$ are preferably hydrogen and R$^{22F}$ is preferably hydrogen, methyl, ethyl or phenyl, in particular hydrogen. Preference is given to complexes of the ligands F-XIX with the transition metals Fe, Co or Ni, in particular Fe. Particular preference is given to 2,6-diacetylpyridinebis(2,4-dimethylphenylimine) iron dichloride, 2,6-diacetylpyridinebis(2,4,6-trimethylphenylimine)iron dichloride, 2,6-diacetylpyridinebis(2-chloro-6-methylphenylimine)iron dichloride, 2,6-diacetylpyridinebis(2,6-diisopropylphenylimine)iron dichloride, 2,6-diacetylpyridinebis(2,6-dichlorophenylimine)iron dichloride, 2,6-pyridinedicarboxaldehydebis(2,6-diisopropylphenylimine)iron dichloride, 2,6-diacetylpyridinebis(2,4-dimethylphenylimine)cobalt dichloride, 2,6-diacetylpyridinebis(2,4,6-trimethylphenylimine)cobalt dichloride, 2,6-diacetylpyridinebis(2-chloro-6-methylphenylimine)cobalt dichloride, 2,6-diacetylpyridinebis(2,6-diisopropylphenylimine)cobalt dichloride, 2,6-diacetylpyridinebis(2,6-dichlorophenylimine)cobalt dichloride, and 2,6-pyridinedicarboxaldehydebis(2,6-diisopropylphenylimine)cobalt dichloride.

Iminophenoxide complexes can also be used as catalysts D). The ligands of these complexes can be prepared, for example, from substituted or unsubstituted salicylaldehydes and primary amines, in particular substituted or unsubstituted arylamines. Transition metal complexes with pi ligands having one or more heteroatoms in the pi system, for example the boratabenzene ligand, the pyrrolyl anion or the phospholyl anion, can also be used as catalysts D).

Further complexes suitable as catalysts D) include those which have bidentate or tridentate chelating ligands. In such ligands, for example, an ether function is linked to an amine or amide function or an amide is linked to a heteroaromatic such as pyridine.

Such combinations of components A) and D) enable, for example, bimodal products to be prepared or comonomers to be generated in situ. Preference is given to using at least one monocyclopentadienyl complex A) in the presence of at least one further catalyst D) customary for the polymerization of olefins and if desired, one or more activating compounds C). Here, depending on the catalyst combinations A) and D), one or more activating compounds C) may be advantageous. The polymerization catalysts D) can likewise be supported and can be used simultaneously or in any order with the complex A) of the present invention. For example, the monocyclopentadienyl complex A) and the polymerization catalysts D) can be applied together to a support B) or different supports B). It is also possible to use mixtures of various catalysts as component D). The molar ratio of transition metal complex A) to polymerization catalyst D) is usually in the range from 1:100 to 100:1, preferably from 1:10 to 20:1 and particularly preferably from 1:1 to 10:1.

The catalyst system may further comprise, as additional component E), a metal compound of the formula (XX),

$$M^G(R^{1G})_{r^G}(R^{2G})_{s^G}(R^{3G})_{t^G} \quad (XX)$$

where

M$^G$ is Li, Na, K, Be, Mg, Ca, Sr, Ba, boron, aluminum, gallium, indium, thallium, zinc, in particular Li, Na, K, Mg, boron, aluminum or Zn, R$^{1G}$ is hydrogen, C$_1$-C$_{10}$-alkyl, C$_6$-C$_{15}$-aryl, alkylaryl or arylalkyl each having from 1 to 10 carbon atoms in the alkyl part and from 6 to 20 carbon atoms in the aryl part, R$^{2G}$ and R$^{3G}$ are each hydrogen, halogen, C$_1$-C$_{10}$-alkyl, C$_6$-C$_{15}$-aryl, alkylaryl, arylalkyl or alkoxy each having from 1 to 20 carbon atoms in the alkyl radical and from 6 to 20 carbon atoms in the aryl radical, or alkoxy with C$_1$-C$_{10}$-alkyl or C$_6$-C$_{15}$-aryl, r$^G$ is an integer from 1 to 3 and s$^G$ and t$^G$ are integers from 0 to 2, with the sum r$^G$+s$^G$+t$^G$ corresponding to the valence of M$^G$, where the component E) is not identical to the component C). It is also possible to use mixtures of various metal compounds of the formula (XX).

Among the metal compounds of the formula (XX), preference is given to those in which
$M^G$ is lithium, magnesium, boron or aluminum and
$R^{1G}$ is $C_1$-$C_{20}$-alkyl.

Particularly preferred metal compounds of the formula (XX) are methyllithium, ethyllithium, n-butyllithium, methylmagnesium chloride, methylmagnesium bromide, ethylmagnesium chloride, ethylmagnesium bromide, butylmagnesium chloride, dimethylmagnesium, diethylmagnesium, dibutylmagnesium, n-butyl-n-octylmagnesium, n-butyl-n-heptylmagnesium, in particular n-butyl-octylmagnesium, tri-n-hexylaluminum, triisobutylaluminum, tri-n-butylaluminum, triethylaluminum, dimethylaluminum chloride, dimethylaluminum fluoride, methylaluminum dichloride, methylaluminum sesquichloride, diethylaluminum chloride and trimethylaluminum and mixtures thereof. The partial hydrolysis products of aluminum alkyls with alcohols can also be used.

When a metal compound E) is used, it is preferably present in the catalyst system in such an amount that the molar ratio of $M^G$ from formula (XX) to transition metal from monocyclopentadienyl compound A) is from 2 000:1 to 0.1:1, preferably from 800:1 to 0.2:1 and particularly preferably from 100:1 to 1:1.

In general, the catalyst solid together with the further metal compound E) of the formula (XX), which may be different from the metal compound or compounds E) used in the preparation of the catalyst solid, is used as constituent of a catalyst system for the polymerization or copolymerization of olefins. It is also possible, particularly when the catalyst solid does not contain any activating component C), for the catalyst system to further comprise, in addition to the catalyst solid, one or more activating compounds C) which are identical to or different from any activating compounds C) present in the catalyst solid.

To prepare the catalyst systems of the present invention, preference is given to immobilizing at least one of the components A) and/or C) on the support B) by physisorption or by means of chemical reaction, i.e. covalent binding of the components, with reactive groups of the support surface. The order in which the support component B), the component A) and any component C) are combined is immaterial. The components A) and C) can be added independently of one another or simultaneously or in premixed form to B). After the individual process steps, the solid can be washed with suitable inert solvents such as aliphatic or aromatic hydrocarbons.

In a preferred embodiment the monocyclopentadienyl complex A) is brought into contact with the activating compound C) in a suitable solvent, usually giving a soluble reaction product, an adduct or a mixture. The preparation obtained in this way is then brought into contact with the support B), which may have been pretreated, and the solvent is completely or partly removed. This preferably gives a solid in the form of a free-flowing powder. Examples of the industrial implementation of the above process are described in WO 96/00243, WO 98/40419 or WO 00/05277. A further preferred embodiment comprises firstly applying the activating compound C) to the support B) and subsequently bringing this supported activating compound into contact with the monocyclopentadienyl complex A).

The component D) can likewise be reacted in any order with the components A) and, if desired, B), C) and E). Preference is given to bringing D) firstly into contact with component C) and then dealing with the components A) and B) and any further C) as described above. In another preferred embodiment, a catalyst solid is prepared from the components A), B) and C) as described above and this is brought into contact with the component E) during, at the beginning of or shortly before the polymerization. Preference is given to E) firstly being brought into contact with the (olefin to be polymerized and the catalyst solid comprising the components A), B) and C) as described above subsequently being added. The monocyclopentadienyl complex A) can be brought into contact with the component(s) C) and/or D) either before or after being brought into contact with the olefins to be polymerized. Preactivation using one or more components C) prior to mixing with the olefin and further addition of the same or different components C) and/or D) after the mixture has been brought into contact with the olefin is also possible. Preactivation is generally carried out at 10-100° C., in particular 20-80° C.

It is also possible for the catalyst system firstly to be prepolymerized with α-olefins, preferably linear $C_2$-$C_{10}$-1-alkenes and in particular ethylene or propylene, and the resulting prepolymerized catalyst solid then to be used in the actual polymerization. The mass ratio of catalyst solid used in the prepolymerization to monomer to be polymerized onto it is usually in the range from 1:01 to 1:1 000, preferably from 1:1 to 1:200.

Furthermore, a small amount of an olefin, preferably an x-olefin, for example vinylcyclohexane, styrene or phenyldimethylvinylsilane, as modifying component, an antistatic or a suitable inert compound such as a wax or oil can be added as additive during or after the preparation of the catalyst system. The molar ratio of additives to transition metal compound B) is usually from 1:1 000 to 1 000:1, preferably from 1:5 to 20:1.

The catalyst systems of the present invention are suitable for the polymerization of olefins and especially for the polymerization of α-olefins, i.e. hydrocarbons having terminal double bonds. Suitable monomers also include functionalized olefinically unsaturated compounds such as acrolein, ester or amide derivatives of acrylic or methacrylic acid, for example acrylates, methacrylates or acrylonitrile, or vinyl esters, for example vinyl acetate. Preference is given to nonpolar olefinic compounds, including aryl-substituted α-olefins. Particularly preferred α-olefins are linear or branched $C_2$-$C_{12}$-1-alkenes, in particular linear $C_2$-$C_{10}$-1-alkenes such as ethene, propene, 1-butene, 1-pentene, 1-hexene, 1-heptene, 1-octene, 1-decene or branched $C_2$-$C_{10}$-1-alkenes such as 4-methyl-1-pentene, conjugated and unconjugated dienes such as 1,3-butadiene, 1,5-hexadiene or 1,7-octadiene or vinylaromatic compounds such as styrene or substituted styrene. It is also possible to polymerize mixtures of various α-olefins. Preference is given to polymerizing at least one olefin selected from the group consisting of ethene, propene, 1-butene, 1-pentene, 1-hexene, 1-heptene, 1-octene and 1-decene.

Suitable olefins also include ones in which the double bond is part of a cyclic structure which can have one or more ring systems. Examples are cyclopentene, cyclohexene, norbornene, tetracyclododecene and methylnorbornene and dienes such as 5-ethylidene-2-norbornene, norbornadiene or ethylnorbornadiene.

Mixtures of two or more olefins can also be polymerized. In contrast to some known iron and cobalt complexes, the transition metal complexes of the present invention display a good polymerization activity even in the case of higher α-olefins, so that their suitability for copolymerization deserves particular emphasis. In particular, the transition metal complexes of the present invention can be used for the polymerization or copolymerization of ethene or propene. As comonomers in the polymerization of ethene, preference is given to using $C_3$-$C_8$-α-olefins or norbornene, in particular 1-butene, 1-pentene, 1-hexene and/or 1-octene. Preference is given to using monomer mixtures containing at least 50 mol % of ethene. Preferred comonomers in the polymerization of propylene are ethene and/or butene.

The polymerization can be carried out in a known manner in bulk, in suspension, in the gas phase or in a supercritical medium in the customary reactors used for the polymerization of olefins. It can be carried out batchwise or preferably continuously in one or more stages. High-pressure polymerization processes in tube reactors or autoclaves, solution processes, suspension processes, stirred gas-phase processes or gas-phase fluidized-bed processes are all possible.

The polymerizations are usually carried out at from −60 to 350° C. under pressures of from 0.5 to 4 000 bar at mean residence times of from 0.5 to 5 hours, preferably from 0.5 to 3 hours. The advantageous pressure and temperature ranges for carrying out the polymerizations usually depend on the polymerization method. In the case of high-pressure polymerization processes, which are usually carried out at pressures of from 1 000 to 4 000 bar, in particular from 2 000 to 3 500 bar, high polymerization temperatures are generally also set. Advantageous temperature ranges for these high-pressure polymerization processes are from 200 to 320° C., in particular from 220 to 290° C. In the case of low-pressure polymerization processes, a temperature which is at least a few degrees below the softening temperature of the polymer is generally set. These polymerization processes are preferably carried out at from 50 to 180° C., preferably from 70 to 120° C. In the case of suspension polymerization, the polymerization is usually carried out in a suspension medium, preferably an inert hydrocarbon such as isobutane or a mixture of hydrocarbons, or else in the monomers themselves. The polymerization temperatures are generally in the range from −20 to 115° C., and the pressure is generally in the range from 1 to 100 bar. The solids content of the suspension is generally in the range from 10 to 80%. The polymerization can be carried out batchwise, e.g. in stirring autoclaves, or continuously, e.g. in tube reactors, preferably in loop reactors. Particular preference is given to employing the Phillips P F process as described in U.S. Pat. Nos. 3,242,150 and 3,248,179. The gas-phase polymerization is generally carried out at from 30 to 125° C.

Among the abovementioned polymerization processes, particular preference is given to gas-phase polymerization, in particular in gas-phase fluidized-bed reactors, solution polymerization and suspension polymerization, in particular in loop reactors and stirred tank reactors. The gas-phase polymerization can also be carried out in the condensed or supercondensed phase, in which part of the circulating gas is cooled to below the dew point and is recirculated as a two-phase mixture to the reactor. It is also possible to use a multizone reactor in which two polymerization zones are linked to one another and the polymer is passed alternately through these two zones a number of times. The two zones can also have different polymerization conditions. Such a reactor is described, for example, in WO 97/04015. The different or identical polymerization processes can also, if desired, be connected in series so as to form a polymerization cascade, for example in the Hostalen process. A parallel reactor arrangement using two or more identical or different processes is also possible. Furthermore, molar mass regulators, for example hydrogen, or customary additives such as antistatics can also be used in the polymerizations.

The monocyclopentadienyl complexes of the present invention and the catalyst systems in which they are present can also be prepared by means of combinations of methods or their polymerization activity can be tested with the aid of these combined methods.

The process of the present invention allows polymers of olefins to be prepared. The term "polymerization" as used here in the description of the present invention encompasses both polymerization and oligomerization, i.e. oligomers and polymers having molar masses Mw in the range from about 56 to 10 000 000 can be produced by this process.

Owing to their good mechanical properties, the olefin polymers prepared using the catalyst system of the present invention are particularly useful for the production of films, fibers and moldings.

The catalyst systems of the present invention give polymers having molar masses which are lower than those obtained using catalyst systems which do not possess an aryl substituent. In addition, the catalyst systems of the present invention display very high activities.

EXAMPLES

All syntheses and polymerizations were carried out under a protective nitrogen atmosphere.

The density, [g/cm$^3$] was determined in accordance with ISO 1183.

The Staudinger index ($\eta$)[dl/g] was determined using an automatic Ubbelohde viscometer (Lauda PVS 1) in decalin as solvent at 130° C. (ISO1628 at 130° C., 0.001 g/ml of decalin).

The NMR spectra were measured on a Bruker DRX 200 ($^1$H, 200.13 MHz). In $^1$H-NMR spectra, the signal of the incompletely deuterated part of the solvent used served as internal standard. All signals were calibrated to the appropriate literature values.

Mass spectra were recorded on a Finnigan MAT 8230, and high-resolution mass spectra were measured on a Micromass CTD ZAB-2F V spectrometer.

Abbreviations in the tables below:

Cat. catalyst t(poly) polymerization time polymer amount of polymer formed density polymer density prod. productivity of the catalyst system in g of polymer obtained per mmol of catalyst (chromium complex) used per hour hexene whether or not hexene is present during the polymerization Example 1

1.1. Preparation of 2-methyl-3-(trimethylsilyloxy)cyclopent-2-enone 37.8 g (240 mmol) of hexamethyldisilazane were added to a mixture of 7.8 g (70 mmol) of 2-methylcyclopentane-1,3-dione and 0.29 g (4.4 mmol) of imidazole and the mixture was subsequently heated at 120° C. for 2 hours. The mixture was allowed to cool to room temperature while stirring and all volatile components were distilled off. Distillation at 60-63° C. and 3×10$^{-3}$ mbar gave 12.7 g (68 mmol, 98%) of 2-methyl-3-(trimethylsilyloxy)cyclopent-2-enone as a colorless liquid.

NMR $^1$H (200, 13 MHZ, CDCl$_3$): 0.26 (9H, s, Me$_3$Si); 1.52 (3H, s, Me); 2.47-2.34 (4H, m, CH$_2$). NMR $^1$H (50, 1 MHZ,

CDCl$_3$): 0.0 (Me$_3$Si); 5.3 (Me); 25.6 (CH$_2$); 32.9 (CH$_2$); 120.1 (C$_{alkene}$); 180.9 (C$_{alkene\text{-}OTMS}$); 205.9 (C—O).

1.2. Preparation of 2-methyl-3-(8-quinolyl)cyclopent-2-enone

A mixture of 38.7 g (186 mmol) of 8-bromoquinoline and 250 ml of tetrahydrofuran was cooled to −80° C., and 74.4 ml of n-butyllithium (2.5 M in hexane, 186 mmol) were subsequently added while stirring. The mixture was stirred for a further 15 minutes and 49.9 g (186 mmol) of 2-methyl-3-(trimethylsilyloxy)cyclopent-2-enone were added while stirring. The mixture was allowed to warm to room temperature while stirring and stirring was continued for a further one hour. The reaction mixture was then hydrolyzed by means of a mixture of 40 g of ice and 30 ml of concentrated hydrochloric acid and the mixture obtained in this way was refluxed for 3 hours. The mixture was allowed to cool to room temperature while stirring and ammonia solution was added until a pH of 12 had been reached. The aqueous phase was then separated off from the organic phase and the aqueous phase was extracted twice with diethyl ether. The organic phases were combined, dried over magnesium sulfate, filtered and the solvent was distilled off. The residue obtained in this way was distilled at 119-139° C. and 2×10$^{-2}$ mbar to give 31.1 g (139.3 mmol, 74.9%) of 2-methyl-3-(8-quinolyl)cyclopent-2-enone.

NMR $^1$H (200, 13 MHZ, CDCl$_3$): 1.69 (3H, t, Me); 2.58 (2H, m, CH$_2$); 3.12 (2H, m, CH$_2$); 7.39 (1H, dd, H$_3$); 7.47-7.60 (2H, m, CH$_{quinolyl}$); 7.82 (1H, dd, CH$_{quinolyl}$); 8.16 (1H, dd, H$_4$); 8.87 (1H, dd, H$_2$). MS (EI), m/e (%): 223 (8) [M$^+$]; 195 (32) [M$^+$-2CH$_2$]; 180(100) [M+-2CH$_2$—CH$_3$].

1.3. Preparation of 3-hydroxy-2-methyl-3-phenyl-1-(8-quinolyl)cyclopentene

A mixture of 2.4 g (10.75 mmol) of 2-methyl-3-(8-quinolyl)cyclopent-2-enone and 100 ml of tetrahydrofuran was cooled to −90° C., and 7.2 ml of phenyllithium (1.8 M in cyclohexane/diethyl ether, 12.9 mmol) were subsequently added while stirring. The mixture was stirred for a further one hour at this temperature and 1 ml of ethyl acetate was then added. The mixture was then allowed to warm to room temperature while stirring, refluxed for 10 minutes, cooled to room temperature and 100 ml of water were then added. The aqueous phase was then separated off from the organic phase and the aqueous phase was extracted twice with diethyl ether. The organic phases were combined, dried over magnesium sulfate, filtered and the solvent was distilled off. The residue was dissolved in 5 ml of toluene and then admixed with 80 ml of hexane. The precipitate formed was filtered off and dried. This gave 1.874 g (6.22 mmol, 57.9% yield) of 3-hydroxy-2-methyl-3-phenyl-1-(8-quinolyl)cyclopentene.

NMR $^1$H (200, 13 MHZ, CDCl$_3$): 1.48 (3H, m, Me); 2.57 (2H, m, CH$_2$); 2.98 (1H, m, CH$_2$); 3.2 (1H, m, CH$_2$); 4.31 (1H, s, OH); 7.39 (1H, dd, H$_3$); 7.25-7.81 (9H, m, CH$_{quinolyl+phenyl}$); 8.16 (1H, dd, H$_4$); 8.88 (1H, dd, H$_2$).

1.4. Preparation of 2-methyl-3-phenyl-1-(8-quinolyl)cyclopentadiene

A mixture of 5 ml of water and 5 ml of concentrated hydrochloric acid was added to a solution of 1.717 g (5.7 mmol) of 3-hydroxy-2-methyl-3-phenyl-1-(8-quinolyl)cyclopentene in 100 ml of tetrahydrofuran. The mixture was stirred at room temperature for 90 minutes and ammonia solution was then added until a pH of 12 had been reached. The aqueous phase was then separated off from the organic phase and the aqueous phase was extracted twice with diethyl ether. The organic phases were combined, dried over magnesium sulfate, filtered and the solvent was distilled off. The residue obtained in this way was distilled at 157-170° C. and 2×10$^{-2}$ mbar to give 1.12 g (3.95 mmol, 69.3%) of 2-methyl-3-phenyl-1-(8-quinolyl)cyclopentadiene.

NMR $^1$H (200, 13 MHZ, CDCl$_3$): 1.2 (3H, d, Me); 2.01 (3H, m, Me); 2.10 (3H, m, Me); 3.65 (2H, m, CH$_2$); 3.9 (2H, m, CH$_2$); 4.78 (1H, s, CHMe); 6.58 (1H, m, CpH); 6.64 (1H, m, CpH); 7.01 (1H, m, CpH); 7.03 (1H, m, CpH); 7.23-7.87 (27H, m, CH$_{quinolyl+phenyl}$); 8.13-8.22 (3H, m, H$_4$); 8.97-9.05 (3H, m, H$_2$).

1.5. Preparation of (2-methyl-3-phenyl-1-(8-quinolyl)cyclopentadienyl)chromium dichloride

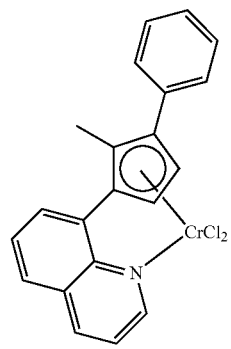

A solution of 1.09 g (3.85 mmol) of 2-methyl-3-phenyl-1-(8-quinolyl)cyclopentadiene in 40 ml of tetrahydrofuran was added to a suspension of 0.157 g (3.85 mmol) of potassium hydride in 20 ml of tetrahydrofuran. After the addition was complete, the reaction mixture was stirred at room temperature for 6 hours and was subsequently added to a solution of 1.44 g (3.85 mmol) of chromium trichloride tris(tetrahydrofuran) in 50 ml of tetrahydrofuran while stirring. The mixture was stirred at room temperature for a further 12 hours and the solvent was then distilled off and the residue was washed 3 times with hexane and 3 times with toluene. The soluble material in the residue obtained in this way was taken up in methylene chloride and filtered. The filtrate was freed of solvent, washed and dried under reduced pressure. This gave 0.969 g (2.39 mmol) of (2-methyl-3-phenyl-1-(8-quinolyl) cyclopentadienyl)chromium dichloride (62%).

NMR $^1$H (200, 13 MHZ, CDCl$_3$): −53.3 (1H, H$_4$); −16.5 (1H, H$_{5\text{-}7}$); 11.2 (3H, Me); 14.8 (1H, H$_5$); 49.4 (1H, H$_3$).

MS (EI), m/e (%):404 (100) [M+]; 369 (76) [M+-Cl]; 332; (92) [M+-2HCl]; 280 (48) [M+-2HCl—Cr].

Example 2

2.1. Preparation of 3-hydroxy-2-methyl-3-(4-benzotrifluoride)-1-(8-quinolyl)cyclopentene A solution of 3.51 g (15.6 mmol) of 4-bromobenzotrifluoride in 80 ml of tetrahydrofuran was cooled to −90° C., and 6.2 ml of n-butyllithium (2.5 M in hexane, 15.6 mmol) were subsequently added while stirring. After stirring for 15 minutes at this temperature, a solution of 2.9 g (13 mmol) of 2-methyl-3-(8-quinolyl)cyclopent-2-enone (see Example 1.2) in 40 ml of tetrahydrofuran was added while stirring. The mixture was stirred for a further one hour at this temperature and 1 ml of ethyl acetate was then added. The mixture was then allowed to warm to room temperature while stirring and 100 ml of water was subsequently added. The aqueous phase was then separated off from the organic phase and the aqueous phase was extracted twice with diethyl ether. The organic phases were combined, dried over magnesium sulfate, filtered and the solvent was distilled off. The residue was dissolved in 5 ml of toluene and then admixed with 80 ml of hexane. The precipitate formed was filtered off and dried. This gave 2.69 g (7.28 mmol) of 3-hydroxy-2-methyl-3-(4-benzotrifluoride)-1-(8-quinolyl)cyclopentene. A second fraction was obtained by cooling the mother liquor (1.42 g, 3.84 mmol, total yield: 85.4%).

NMR $^1$H (200, 13 MHZ, CDCl$_3$): 1.42 (3H, m, Me); 2.52 (2H, m, CH$_2$); 2.98 (1H, m, CH$_2$); 3.18 (1H, m, CH$_2$); 4.10 (1H, s, OH); 7.39 (1H, dd, H$_3$); 7.56-7.84 (7H, m, CH$_{quinolyl+aryl}$); 8.18 (1H, dd, H$_4$); 8.89 (1H, dd, H$_2$).

MS (EI), m/e (%): 369 (9) [M$^+$]; 351 (100) [M$^+$-H$_2$O]; 336 (12) [M$^+$-H$_2$O-Me]; 181 (72) [M$^+$-H$_2$O-Me-quinolyl -CH$_2$].

2.2. Preparation of 2-methyl-3-(4-benzotrifluoride)-1-(8-quinolyl)cyclopentadiene A mixture of 5 ml of water and 5 ml of concentrated hydrochloric acid was added to a solution of 3.61 g (9:8 mmol) of 3-hydroxy-2-methyl-3-(4-benzotrifluoride)-1-(8-quinolyl)cyclopentene in 100 ml of tetrahydrofuran. The mixture was stirred at room temperature for 90 minutes and ammonia solution was then added until a pH of 12 had been reached. The aqueous phase was then separated off from the organic phase and the aqueous phase was extracted twice with diethyl ether. The organic phases were combined, dried over magnesium sulfate, filtered and the solvent was distilled off. The residue obtained in this way was distilled at 169-176° C. and 2×10$^{-2}$ mbar to give 2.09 g (5.9 mmol, 60.2%) of 2-methyl-3-(4-benzotrifluoride)-1-(8-quinolyl)cyclopentadiene.

NMR $^1$H (200, 13 MHZ, CDCl$_3$): 1.13 (3H, d, Me); 1.97 (3H, m, Me); 2.03 (3H, m, Me); 3.62 (2H, m, CH$_2$); 3.87 (2H, m, CH$_2$); 4.81 (1H, q, CHMe); 6.59 (1H, m, CpH); 6.66 (1H, m, CpH); 7.07 (1H, m, CpH); 7.26 (1H, m, CpH); 7.31-7.88 (24H, m, CH$_{quinolyl+aryl}$); 8.14-8.24 (3H, m, H$_4$); 8.93-9.02 (3H, m, H$_2$).

MS (EI), m/e (%): 351 (100) [M$^+$]; 167 (72) [M$^+$-F$_3$CC$_6$H$_4$-C$_3$H$_3$].

2.3. Preparation of (2-methyl-3-(4-benzotrifluoride)-1-(8-quinolyl)cyclopentadienyl)chromium dichloride

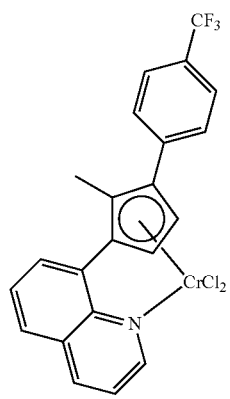

A solution of 2.09 g (5.95 mmol) of 2-methyl-3-(4-benzotrifluoride)-1-(8-quinolyl)cyclopentadiene in 40 ml of tetrahydrofuran was added to a suspension of 0.242 g (5.95 mmol) of potassium hydride in 20 ml of tetrahydrofuran. After the addition was complete, the reaction mixture was stirred at room temperature for 6 hours and subsequently added to a solution of 2.23 g (5.95 mmol) of chromium trichloride tris(tetrahydrofuran) in 50 ml of tetrahydrofuran while stirring. The mixture was stirred at room temperature for a further 12 hours and the solvent was then distilled off and the residue washed 3 times with hexane and 3 times with toluene. The residue obtained in this way was extracted 3 times with methylene chloride and filtered off. The combined methylene chloride extracts were freed of solvent, washed and dried under reduced pressure. This gave 1.58 g (3.34 mmol) of (2-methyl-3-(4-benzotrifluoride)-1-(8-quinolyl) cyclopentadienyl)chromium dichloride (56.1%).

NMR $^1$H (200, 13 MHZ, CDCl$_3$): −54.1 (1H, H$_4$); −17.1 (1H, H$_5$); 13.5 (3H, Me); 14.9 (1H, H$_6$); 48.8 (1H, H$_3$).

MS (EI), m/e (%): 472 (100) [M$^+$]; 437 (82) [M$^+$-Cl]; 400 (49) [M$^+$-2HCl]; 380 (22) [M$^+$-2HCl—Cr—HF]; 348 (23) [M$^+$-2HCl—Cr].

Example 3 (Comparative Example)

3.1. Preparation of 2-methyl-3-pentyl-1-(8-quinolyl)cyclopentadiene

A solution of 6.8 g (32 mmol) of 8-bromoquinoline in 90 ml of tetrahydrofuran was cooled to −90° C., and 12.8 ml of n-butyllithium (2.5 M in hexane, 32 mmol) were subsequently added while stirring. After stirring for 15 minutes at this temperature, 5.3 g (32 mmol) of 2-methyl-3-pentylcyclopent-2-enone (dihydroisojasmone) were added while stirring. The mixture was stirred at this temperature for a further one hour, allowed to warm to room temperature and then refluxed for one hour. After cooling to room temperature, a mixture of 30 g of ice and 30 g of concentrated hydrochloric acid was added and the resulting mixture was refluxed for 2 hours. The mixture was allowed to cool to room temperature while stirring and ammonia solution was added until a pH of 12 had been reached. The aqueous phase was then separated off from the organic phase and the aqueous phase was extracted twice with diethyl ether. The organic phases were combined, dried over magnesium sulfate, filtered and the solvent was distilled off. The residue was dissolved in 5 ml of toluene and then admixed with 80 ml of hexane. The precipitate formed was filtered off and dried. The residue obtained in this way was distilled at >110° C. and 1×10$^{-2}$ mbar to give 2.6 g of 2-methyl-3-pentyl-1-(8-quinolyl)cyclopentadiene.

3.2. Preparation of (2-methyl-3-pentyl-1-(8-quinolyl) cyclopentadienyl)chromium dichloride

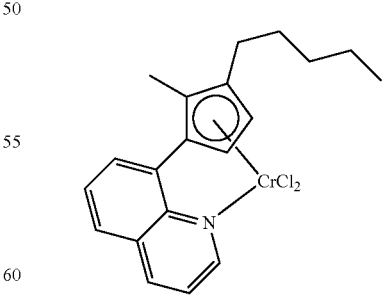

A solution of 0.5 g (1.81 mmol) of 2-methyl-3-pentyl-1-(8-quinolyl)cyclopentadiene in 20 ml of tetrahydrofuran was added to a suspension of 0.07 g (1.81 mmol) of potassium hydride in 20 ml of tetrahydrofuran. After the addition was complete, the reaction mixture was stirred at room temperature for 16 hours and subsequently added to a solution of 0.67 g (1.81 mmol) of chromium trichloride tris(tetrahydrofuran) in 20 ml of tetrahydrofuran while stirring. The mixture was stirred at room temperature for a further 16 hours, and precipitated product was then filtered off and washed twice with hexane. This gave 0.45 g (1.12 mmol) of (2-methyl-3-pentyl-1-(8-quinolyl)cyclopentadienyl)chromium dichloride (62%).

Examples 4-7

Polymerization

The polymerizations were carried out at 40° C. under argon in a 1 l four-necked flask provided with contact thermometer, stirrer with Teflon blade, heated mantle and gas inlet tube. The appropriate amount of Mao (10% strength solution in toluene, Cr:Al as in Table 1) was added to a solution of the amount indicated in Table 1 of the appropriate complex in 250 ml of toluene and the mixture was heated to 40° C. on a water bath.

In the ethylene homopolymerizations, ethylene was passed through the solution at a flow rate of from about 20 to 40 l/h at atmospheric pressure. In the case of the ethylene/1-hexene copolymerization, 3 ml of hexene were placed in the flask shortly before addition of ethylene and ethylene was subsequently passed through the mixture at a flow rate of from about 20 to 40 l/h at atmospheric pressure. The remaining amount of hexene (6 ml) was added via a dropping funnel over a period of 15 minutes. After maintaining a constant ethylene flow for the time indicated in Table 1, the polymerization was stopped by addition of methanolic HCl solution (15 ml of concentrated hydrochloric acid in 50 ml of methanol). 250 ml of methanol were subsequently added and the white polymer formed was filtered off, washed with methanol and dried at 70° C.

Y is a substituent which is bound to Cp and comprises at least one uncharged donor comprising at least one atom of group 15 or 16 of the Periodic Table;

$M^A$ is titanium, zirconium, hafnium, vanadium, niobium, tantalum, chromium, molybdenum or tungsten, or an element of group 3 or a lanthanide of the Periodic Table;

m is 1, 2 or 3;

$X^A$ independently of one another, are fluorine, chlorine, bromine, iodine, hydrogen, a $C_1$-$C_{10}$-alkyl, a $C_2$-$C_{10}$-alkenyl, a $C_6$-$C_{20}$-aryl, an alkylaryl comprising 1-10 carbon atoms in the alkyl part and 6-20 carbon atoms in the aryl part, $NR^{23A}R^{24A}$, $OR^{23A}$, $SR^{23A}$, $SO_3R^{23A}$, $OC(O)R^{23A}$, CN, SCN, β-diketonate, CO, $BF_4^-$, $PF_6^-$ or bulky noncoordinating anions, or two radicals $X^A$ form a substituted or unsubstituted diene ligand, or two or more $X^A$ radicals may be joined to one another;

$R^{23A}$-$R^{24A}$ independently of one another, are hydrogen, a $C_1$-$C_{20}$-alkyl, a $C_2$-$C_{20}$-alkenyl, a $C_6$-$C_{20}$-aryl, an alkylaryl comprising 1 to 10 carbon atoms in the alkyl part and 6-20 carbon atoms in the aryl part, or $SiR^{25A}_3$, wherein $R^{23A}$-$R^{24A}$ may also be substituted by halogens or nitrogen- and oxygen-containing groups, or two $R^{23A}$-$R^{24A}$ radicals optionally can be joined to form a five- or six-membered ring;

$R^{25A}$ independently of one another, are hydrogen, a $C_1$-$C_{20}$-alkyl, a $C_2$-$C_{20}$-alkenyl, a $C_6$-$C_{20}$-aryl, an alkylaryl comprising from 1 to 10 carbon atoms in the alkyl part and 6-20 carbon atoms in the aryl part, wherein two $R^{25A}$ radicals optionally can join to form a five- or six-membered ring; and n is 1, 2, or 3.

3. The monocyclopentadienyl complex as claimed in claim 2, wherein $X^A$ is a 1,3-diene ligand.

TABLE 1

| | | | | Polymerization results | | | | | |
|---|---|---|---|---|---|---|---|---|---|
| Ex. | Cat. from Ex. | Amount of cat. [mg] ([μmol]) | Cr:Al | t(poly) [min] | Hexene | Polymer [g] | Prod. [g/(mmol M · h)] | Eta-value [dl/g] | Density [g/cm³] |
| 4 | 2 | 13.3 (28.1) | 1:500 | 15 | no | 13.3 | 1895 | 1.08 | n.d. |
| 5 | 3 | 10.2 (25.8) | 1:350 | 30 | no | 3.8 | 738 | 10.4 | 0.921 |
| 6 | 2 | 11.5 (24.3) | 1:500 | 15 | yes | 13.8 | 2263 | 0.79 | 0.917 |
| 7 | 1 | 12.1 (29.9) | 1:500 | 15 | yes | 13.1 | 1754 | 0.55 | 0.909 |

We claim:

1. A monocyclopentadienyl complex comprising a structural feature of formula Cp-$Y_m M^A$ (I), wherein:

Cp is a cyclopentadienyl system comprising an aryl substituent;

Y is a substituent which is bound to Cp and comprising at least one uncharged donor comprising at least one atom of group 15 or 16 of the Periodic Table;

$M^A$ is titanium, zirconium, hafnium, vanadium, niobium, tantalum, chromium, molybdenum or tungsten, or an element of group 3 or a lanthanide of the Periodic Table; and m is 1, 2 or 3.

2. A monocyclopentadienyl complex comprising formula Cp-$Y_m M^A X^A_n$ (V), wherein:

Cp is a cyclopentadienyl system comprising an aryl substituent;

4. The monocyclopentadienyl complex as claimed in claim 1, wherein Y comprises group -$Z_k$-A-; the group -$Z_k$-A- together with the cyclopentadienyl system Cp and $M^A$ form a monocyclopentadienyl complex comprising formula Cp-$Z_k$-A-$M^A$ (II), wherein CP-$Z_k$-A comprises:

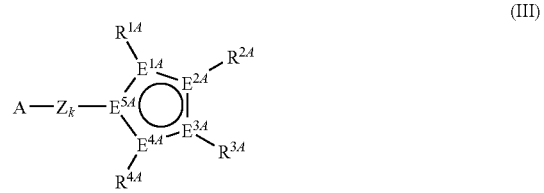

(III)

wherein:

$E^{1A}$-$E^{5A}$ are each carbon or a heteroatom, with the proviso that not more than one $E^{1A}$-$E^{5A}$ are phosphorus;

$R^{1A}$-$R^{4A}$ independently of one another, are hydrogen, a $C_1$-$C_{22}$-alkyl, a $C_2$-$C_{22}$-alkenyl, a $C_6$-$C_{22}$-aryl, an alkylaryl comprising 1 to 10 carbon atoms in the alkyl radical and 6-20 carbon atoms in the aryl radical, $NR^{5A}{}_2$, $N(SiR^{5A}{}_3)_2$, $OR^{5A}$, $OSiR^{5A}{}_3$, $SiR^{5A}{}_3$, $BR^{5A}{}_2$, wherein optionally $R^{1A}$-$R^{4A}$ can be substituted by at least one halogen, or two vicinal $R^{1A}$-$R^{4A}$ radicals optionally can be joined to form a five-, six-, or seven-membered ring, or two vicinal $R^{1A}$-$R^{4A}$ radicals optionally can be joined to form a five-, six-, or seven-membered heterocycle ring comprising at least one atom from the group consisting of N, P, O and S, with the proviso that at least one $R^{1A}$-$R^{4A}$ is a $C_1$-$C_{22}$-alkyl, a $C_2$-$C_{22}$-alkenyl, a halogen, a haloalkyl comprising 1-10 carbon atoms, or a haloaryl comprising 1-10 carbon atoms, or a $C_6$-$C_{22}$ aryl, wherein the $C_6$-$C_{22}$ aryl optionally can be substituted by N—, P—, O— or S-containing substituents;

$R^{5A}$ independently of one another, are hydrogen, a $C_1$-$C_{20}$-alkyl, a $C_2$-$C_{20}$-alkenyl, a $C_6$-$C_{20}$-aryl, an alkylaryl comprising from 1 to 10 carbon atoms in the alkyl part and 6-20 carbon atoms in the aryl part, or two geminal radicals that optionally can be joined to form a five- or six-membered ring;

Z is a divalent bridge between A and Cp selected from the group consisting of:

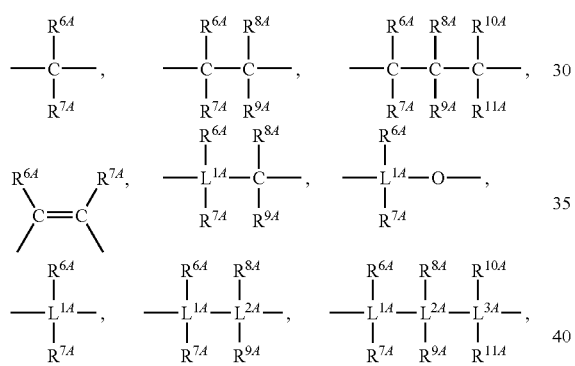

—$BR^{6A}$—, —$BNR^{6A}R^{7A}$—, $AlR^{6A}$—, —Sn—, —O—, —S—, —SO—, —$SO_2$—, —$NR^{6A}$—, —CO—, —$PR^{6A}$— or —$P(O)R^{6A}$, wherein $L^{1A}$-$L^{3A}$ independently of one another, are silicon or germanium;

$R^{6A}$-$R^{11A}$ independently of one another, are hydrogen, a $C_1$-$C_{20}$-alkyl, a $C_2$-$C_{20}$-alkenyl, a $C_6$-$C_{20}$-aryl, an alkylaryl comprising from 1 to 10 carbon atoms in the alkyl part and 6-20 carbon atoms in the aryl part, or $SiR^{12}A_3$, wherein $R^{6A}$-$R^{11A}$ optionally can be substituted by at least one halogen or two geminal or vicinal $R^{6A}$-$R^{11A}$ radicals optionally can be joined to form a five- or six-membered ring;

$R^{12A}$ independently of one another, are hydrogen, a $C_1$-$C_{20}$-alkyl, a $C_2$-$C_{20}$-alkenyl, a $C_6$-$C_{20}$-aryl, a $C_6$-$C_{20}$ alkylaryl comprising from 1 to 10 carbon atoms in the alkyl part and 6-20 carbon atoms in the aryl part, a $C_1$-$C_{10}$-alkoxy, or $C_6$-$C_{10}$-aryloxy, wherein two $R^{12A}$ radicals optionally can be joined to form a five- or six-membered ring;

A is an uncharged donor group comprising at least one atom of group 15 or 16 of the Periodic Table of Elements, or a carbine;

$M^A$ is a metal selected from the group consisting of titanium comprising an oxidation state 3, vanadium, chromium, molybdenum, and tungsten; and k is 0 or 1.

5. The monocyclopentadienyl complex as claimed in claim 4, wherein A is an unsubstituted, substituted, or fused heteroaromatic ring system.

6. The monocyclopentadienyl complex as claimed in claim 2, wherein Y comprises group -$Z_k$-A-; the group -$Z_k$-A together with the cyclopentadienyl system Cp, and $M^A$ forms a monocyclopentadienyl complex comprising formula Cp-$Z_k$-A-$M^A$(II), wherein CP-$Z_k$-A comprises:

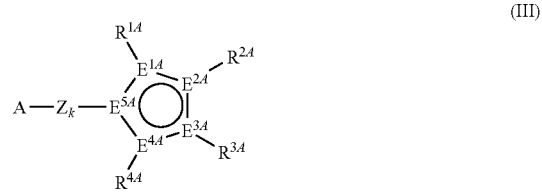

wherein:

$E^{1A}$-$E^{5A}$ are each carbon or a heteroatom, with the proviso that not more than one $E^{1A}$-$E^{5A}$ are phosphorus;

$R^{1A}$-$R^{4A}$ independently of one another, are hydrogen, a $C_1$-$C_{22}$-alkyl, a $C_2$-$C_{22}$-alkenyl, a $C_6$-$C_{22}$-aryl, an alkylaryl comprising 1 to 10 carbon atoms in the alkyl radical and 6-20 carbon atoms in the aryl radical, $NR^{5A}{}_2$, $N(SiR^{5A}{}_3)_2$, $OR^{5A}$, $OSiR^{5A}{}_3$, $SiR^{5A}{}_3$, $BR^{5A}{}_2$, wherein optionally $R^{1A}$-$R^{4A}$ can be substituted by at least one halogen, or two vicinal $R^{1A}$-$R^{4A}$ radicals optionally can be joined to form a five-, six-, or seven-membered ring, or two vicinal $R^{1A}$-$R^{4A}$ radicals optionally can be joined to form a five-, six-, or seven-membered heterocycle ring comprising at least one atom from the group consisting of N, P, O and S, with the proviso that at least one $R^{1A}$-$R^{4A}$ is a $C_1$-$C_{22}$-alkyl, a $C_2$-$C_{22}$-alkenyl, a halogen, a haloalkyl comprising 1-10 carbon atoms, or a haloaryl comprising 1-10 carbon atoms, or a $C_6$-$C_{22}$ aryl, wherein the $C_6$-$C_{22}$ aryl optionally can be substituted by N—, P—, O— or S-containing substituents;

$R^{5A}$ independently of one another, are hydrogen, a $C_1$-$C_{20}$-alkyl, a $C_2$-$C_{20}$-alkenyl, a $C_6$-$C_{20}$-aryl, an alkylaryl comprising from 1 to 10 carbon atoms in the alkyl part and 6-20 carbon atoms in the aryl part, or two geminal radicals that optionally can be joined to form a five- or six-membered ring;

Z is a divalent bridge between A and Cp selected from the group consisting of:

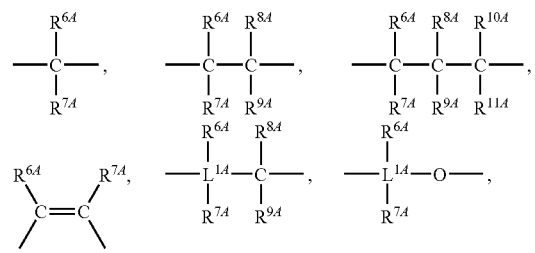

-continued

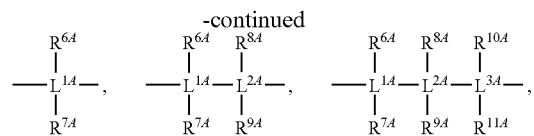

—BR$^{6A}$—, —BNR$^{6A}$R$^{7A}$—, —AlR$^{6A}$—, —Sn—, —O—, —S—, —SO—, —SO$_2$—, —NR$^{6A}$—, —CO—, —PR$^{6A}$— or —P(O)R$^{6A}$, wherein L$^{1A}$-L$^{3A}$ independently of one another, are silicon or germanium;

R$^{6A}$-R$^{11A}$ independently of one another, are hydrogen, a C$_1$-C$_{20}$-alkyl, a C$_2$-C$_{20}$-alkenyl, a C$_6$-C$_{20}$-aryl, an alkylaryl comprising from 1 to 10 carbon atoms in the alkyl part and 6-20 carbon atoms in the aryl part, or SiR$^{12A}{}_3$, wherein R$^{6A}$-R$^{11A}$ optionally can be substituted by at least one halogen or two geminal or vicinal R$^{6A}$-R$^{11A}$ radicals optionally can be joined to form a five- or six-membered ring;

R$^{12A}$ independently of one another, are hydrogen, a C$_1$-C$_{20}$-alkyl, a C$_2$-C$_{20}$-alkenyl, a C$_6$-C$_{20}$-aryl, a C$_6$-C$_{20}$ alkylaryl comprising from 1 to 10 carbon atoms in the alkyl part and 6-20 carbon atoms in the aryl part, a C$_1$-C$_{10}$-alkoxy, or C$_6$-C$_{10}$-aryloxy, wherein two R$^{12A}$ radicals optionally can be joined to form a five- or six-membered ring;

A is an uncharged donor group comprising at least one atom of group 15 or 16 of the Periodic Table of Elements, or a carbine;

M$^A$ is a metal selected from the group consisting of titanium comprising an oxidation state 3, vanadium, chromium, molybdenum, and tungsten; and k is 0 or 1.

7. The monocyclopentadienyl complex as claimed in claim 6, wherein A is an unsubstituted, substituted, or fused heteroaromatic ring system.

8. The monocyclopentadienyl complex as claimed in claim 4, wherein A comprises formula (IVa) or (IVb):

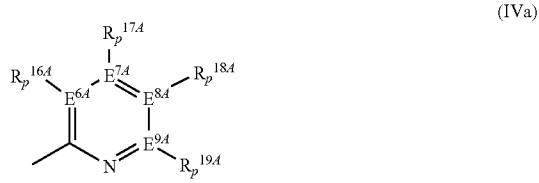

(IVa)

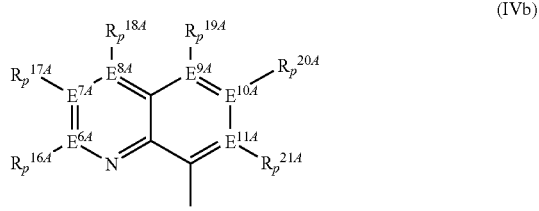

(IVb)

wherein:

E$^{6A}$-E$^{11A}$ independently of one another, are carbon or nitrogen;

R$^{16A}$-R$^{21A}$ independently of one another, are hydrogen, a C$_1$-C$_{20}$-alkyl, a C$_2$-C$_{20}$-alkenyl, a C$_6$-C$_{20}$-aryl, an alkylaryl comprising from 1 to 10 carbon atoms in the alkyl part and 6-20 carbon atoms in the aryl part, or SiR$^{22A}{}_3$, wherein R$^{16A}$-R$^{21A}$ optionally can be substituted by at least one halogen or nitrogen, or two vicinal R$^{16A}$-R$^{21A}$ radicals or R$^{16A}$ and Z optionally can be joined to form a five- or six-membered ring;

R$^{22A}$ independently of one another, are hydrogen, a C$_1$-C$_{20}$-alkyl, a C$_2$-C$_{20}$-alkenyl, a C$_6$-a C$_{20}$-aryl, an alkylaryl comprising from 1 to 10 carbon atoms in the alkyl part and 6-20 carbon atoms in the aryl part, or two R$^{22A}$ radicals optionally can be joined to form a five- or six-membered ring; with the proviso that p is 0 when E$^{6A}$-E$^{11A}$ is nitrogen, and p is 1 when E$^{6A}$-E$^{11A}$ is carbon.

9. The monocyclopentadienyl complex as claimed in claim 5, wherein A comprises formula (IVa) or (IVb):

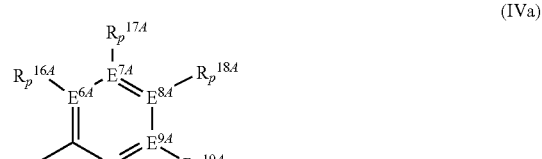

(IVa)

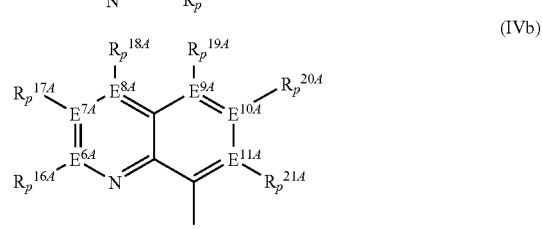

(IVb)

wherein:

E$^{6A}$-E$^{11A}$ independently of one another, are carbon or nitrogen;

R$^{16A}$-R$^{21A}$ independently of one another, are hydrogen, a C$_1$-C$_{20}$-alkyl, a C$_2$-C$_{20}$-alkenyl, a C$_6$-C$_{20}$-aryl, an alkylaryl comprising from 1 to 10 carbon atoms in the alkyl part and 6-20 carbon atoms in the aryl part, or SiR$^{22A}{}_3$, wherein R$^{16A}$-R$^{21A}$ optionally can be substituted by at least one halogen or nitrogen, or two vicinal R$^{16A}$-R$^{21A}$ radicals or R$^{16A}$ and Z optionally can be joined to form a five- or six-membered ring;

R$^{22A}$ independently of one another, are hydrogen, a C$_1$-C$_{20}$-alkyl, a C$_2$-C$_{20}$-alkenyl, a C$_6$-a C$_{20}$-aryl, an alkylaryl comprising from 1 to 10 carbon atoms in the alkyl part and 6-20 carbon atoms in the aryl part, or two R$^{22A}$ radicals optionally can be joined to form a five- or six-membered ring; with the proviso that p is 0 when E$^{6A}$-E$^{11A}$ is nitrogen, and p is 1 when E$^{6A}$-E$^{11A}$ is carbon.

10. The monocyclopentadienyl complex as claimed in claim 4, wherein -Z-A and the aryl substituent are in the 1,3-positions relative to one another.

11. The monocyclopentadienyl complex as claimed in claim 6, wherein -Z-A and the aryl substituent are in the 1,3-positions relative to one another.

12. A catalyst system for olefin polymerization comprising:

A) at least one monocyclopentadienyl complex according to claim 1;

B) optionally, an organic or inorganic support;

C) optionally, one or more activating compounds;

D) optionally, further catalysts for olefin polymerization; and

E) optionally, one or more metal compounds comprising a metal of group 1, 2 or 13 of the Periodic Table.

13. The prepolymerized catalyst system comprising a catalyst system as claimed in claim 12, the catalyst system further comprising one or more linear $C_2$-$C_{10}$ 1-alkenes polymerized onto the catalyst system in a mass ratio of from 1:0.1 to 1:1,000.

14. The process for preparing polyolefins by polymerization or copolymerization of olefins in presence of the catalyst system as claimed in claim 12.

15. The process for preparing polyolefins by polymerization or copolymerization of olefins in presence of the catalyst system as claimed in claim 13.

16. A process for preparing a cyclopentadiene system of formula (VIa)

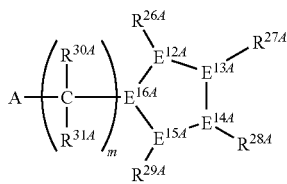

(VIa)

wherein
$E^{12A}$-$E^{16A}$ are each carbon, wherein four adjacent $E^{12A}$-$E^{16A}$ form a conjugated diene system and the remaining $E^{12A}$-$E^{16A}$ bears hydrogen,
$R^{26A}$-$R^{29A}$ independently of one another, are hydrogen, a $C_1$-$C_{20}$-alkyl, a $C_2$-$C_{20}$-alkenyl, a $C_6$-$C_{20}$-aryl, a $C_6$-$C_{20}$ alkylaryl comprising from 1 to 10 carbon atoms in the alkyl part and 6-20 carbon atoms in the aryl part, $NR^{32A}_2$, $N(SiR^{32A}_3)_2$, $OR^{32A}$, $OSiR^{32A}_3$, $BR^{32A}_2$, $SiR^{32A}_3$, wherein $R^{26A}$-$R^{29A}$ optionally can be substituted by at least one halogen or two vicinal $R^{26A}$-$R^{29A}$ radicals that optionally can be joined to form a five- or six-membered ring, or two vicinal $R^{26A}$-$R^{29A}$ radicals optionally can form a heterocycle comprising at least one atom from the group consisting of N, P, O or S;
$R^{30A}$-$R^{31A}$ independently of one another, are a hydrogen, a $C_1$-$C_{20}$-alkyl, a $C_2$-$C_{20}$-alkenyl, a $C_6$-$C_{20}$-aryl, a alkylaryl comprising from 1 to 10 carbon atoms in the alkyl part and 6-20 carbon atoms in the aryl part, or $SiR^{32A}_3$, wherein $R^{30A}$-$R^{31A}$ optionally can be substituted by at least one halogen, and $R^{30A}$ and A, or $R^{31A}$ and A optionally can be joined to form a five- or six-membered ring;
$R^{32A}$ independently of one another, are hydrogen, a $C_1$-$C_{20}$-alkyl, a $C_2$-$C_{20}$-alkenyl, a $C_6$-$C_{20}$-aryl, an alkylaryl comprising from 1 to 10 carbon atoms in the alkyl part and 6-20 carbon atoms in the aryl part, and two geminal $R^{32A}$ radicals optionally can be joined to form a five- or six-membered ring;
m is 0, 1 or 2;
A is an uncharged donor group comprising at least one atom of group 15 or 16 of the Periodic Table of Elements, or a carbine;
the process comprising:
reacting an $(A\text{-}(CR^{29A}R^{30A})_m)^-$ anion with a cyclopentanedione or a silyl ether of an enolised cyclopentanedione.

17. The process of claim 16, wherein A is an unsubstituted, substituted, or fused heteroaromatic ring system.

* * * * *